(12) United States Patent
Jain et al.

(10) Patent No.: US 9,234,020 B2
(45) Date of Patent: Jan. 12, 2016

(54) DERIVATISATION OF ERYTHROPOIETIN (EPO)

(71) Applicant: Lipoxen Technologies Limited, London (GB)

(72) Inventors: Sanjay Jain, London (GB); Peter Laing, London, GA (US); Gregory Gregoriadis, London (GB); Norbert Oskar Rumpf, London (GB)

(73) Assignee: Lipoxen Technologies Limited, London (GB)

( * ) Notice: Subject to any disclaimer, the term of this patent is extended or adjusted under 35 U.S.C. 154(b) by 0 days.

(21) Appl. No.: 14/561,991

(22) Filed: Dec. 5, 2014

(65) Prior Publication Data

US 2015/0158924 A1    Jun. 11, 2015

Related U.S. Application Data

(63) Continuation of application No. 14/313,870, filed on Jun. 24, 2014, now Pat. No. 8,933,026, which is a continuation of application No. 13/646,605, filed on Oct. 5, 2012, now Pat. No. 8,796,207, which is a continuation of application No. 12/375,008, filed as application No. PCT/GB2007/002841 on Jul. 25, 2007, now Pat. No. 8,299,026.

(30) Foreign Application Priority Data

Jul. 25, 2006 (EP) .................................... 06117830

(51) Int. Cl.

| | | |
|---|---|---|
| A61K 38/18 | (2006.01) | |
| A61K 38/00 | (2006.01) | |
| C07K 14/505 | (2006.01) | |
| A61K 47/48 | (2006.01) | |
| C07K 14/535 | (2006.01) | |
| C07K 14/52 | (2006.01) | |
| C07K 14/575 | (2006.01) | |
| A61K 38/46 | (2006.01) | |

(52) U.S. Cl.
CPC ............. *C07K 14/505* (2013.01); *A61K 38/465* (2013.01); *A61K 47/4823* (2013.01); *C07K 14/52* (2013.01); *C07K 14/535* (2013.01); *C07K 14/575* (2013.01); *A61K 38/00* (2013.01); *C12Y 301/21001* (2013.01)

(58) Field of Classification Search
None
See application file for complete search history.

(56) References Cited

U.S. PATENT DOCUMENTS

| | | | |
|---|---|---|---|
| 5,308,617 A | 5/1994 | Halluin | |
| 5,846,951 A | 12/1998 | Gregoriadis | |
| 7,074,755 B2 | 7/2006 | Heavner | |
| 7,128,913 B2 | 10/2006 | Burg et al. | |
| 2004/0082765 A1 | 4/2004 | Nakamura et al. | |

FOREIGN PATENT DOCUMENTS

| | | |
|---|---|---|
| EP | 1219636 A2 | 7/2002 |
| EP | 1681303 A1 | 7/2006 |
| WO | 9105867 A1 | 5/1991 |
| WO | 9222331 A1 | 12/1992 |
| WO | 0187922 A2 | 11/2001 |
| WO | 03055526 A2 | 7/2003 |
| WO | 2005016973 A1 | 2/2005 |
| WO | 2005016974 A1 | 2/2005 |
| WO | 2005092928 A1 | 10/2005 |
| WO | 2006016161 A1 | 2/2006 |
| WO | 2006016168 A2 | 2/2006 |
| WO | 2006090119 A1 | 8/2006 |
| WO | 2008012540 A1 | 1/2008 |

OTHER PUBLICATIONS

Cao(2013)., Trends in Endocrinology and Metabolism, vol. 24, No. 4, pp. 190-199.*
Hayat (2009)., British Journal of Medical Practioners, vol. 2, No. 3, pp. 12-20.*
Fan et al., Exp. Hematol. (2006) 34:1303-1311.
Fernandes et al.; Biochimica et Biophysica Acta (1996) 1293:92-96.
Fernandes et al., Biochimica et Biophysica Acta (1997) 1341:26-34.
Gregoradis et al., FEBS Letters (1993) 315:271-276.
Gregoriadis et al., Int'l J Pharmaceutics (2005) 300(1-2):125-130.
International Search Report for PCT/GB2007/002641, mailed on Mar. 28, 2008, 3 pages.
Jain et al., Biochimica et Biophysica Acta (2003) 1622:42-49.
Jain et al., Drug Delivery Systems and Sciences (2004) 4(2):3-9.
Krystal, Exp. Hematol. (1983) 11(7):649-660.
Park et al., Journal of BioloQical Chemistry (1949) 181:149-151.
Svennerholm, Biochimica et Biophysica Acta (1957)24:604-611.
Wang, International Journal of Pharmaceutics (1999) 185:129-188.
Fiala, et al., "P-glycoprotein-mediated multidrug resistance phenotype of L1210/VCR cells is associated with decreases of oligo-and/or polysaccharide contents," Biochim Biophys Acta, (2003), vol. 1639, No. 3, pp. 213-224.
FDA Prescribing Information EPOGEN PROCRIT, 2005.
FDA Prescribing Information DARBEPOETIN, 2005.

* cited by examiner

*Primary Examiner* — Christine J Saoud
*Assistant Examiner* — Jegatheesan Seharaseyon
(74) *Attorney, Agent, or Firm* — One3 IP Management, P.C.; Dean G. Stathakis; Peter D. Weinstein

(57) ABSTRACT

The present invention relates to a compound which is a polysaccharide derivative of EPO, or of an EPO like protein, wherein the polysaccharide is anionic and comprises between 2 and 200 saccharide units. The present invention also relates to pharmaceutical compositions comprising the novel compounds, and methods for making the novel compounds.

17 Claims, 25 Drawing Sheets

DERIVATISATION OF ERYTHROPOIETIN (EPO)

The present invention is a divisional of U.S. patent application Ser. No. 14/313,870, which is a continuation of U.S. patent application Ser. No. 13/646,605 filed on Oct. 5, 2012, now U.S. Pat. No. 8,796,207, which is a continuation of U.S. patent application Ser. No. 12/375,008 filed on Jan. 23, 2009, now issued as U.S. Pat. No. 8,299,026, which is the national stage entry of PCT/GB2007/002841, filed on Jul. 25, 2007, which claims priority to EP 06117830.7, filed on Jul. 25, 2006, all of which are hereby incorporated by reference.

The present invention relates to novel polysaccharide derivatives of EPO and methods for producing such derivatives. The derivatives are useful for improving the stability, pharmacokinetics and pharmacodynamics of EPO.

Erythropoietin is a glycoprotein hormone and is a cytokine for erythrocyte (red blood cell) precursors in the bone marrow. Also called hematopoietin or hemopoietin, it is produced by the kidney, and regulates red blood cell production.

Erythropoietin is the main regulator of erythropoiesis in the body. (Martindale, 1996). Recombinant human erythropoietin is commercially available in forms known as epoetin alfa and epoetin beta. These are used in the management of anaemia in patients with chronic renal failure. Epoetin gamma is also available. All have the same 165 amino acid sequence, but differ in their glycosylation pattern.

Recombinant human erythropoietin should be used with caution in patients with hypertension, a history of seizures, thrombocytosis, chronic liver failure, ischaemic vascular disease, or in patients with malignant tumors. Epoetin alfa and beta exhibit some differences in their pharmacokinetics, possibly due to differences in glycosylation and in the formulation of the commercial preparations. Epoetin alfa is slowly and incompletely absorbed following subcutaneous injection and a bioavailability of about 10 to 50% relative to intravenous administration has been reported. Epoetin beta is also slowly and incompletely absorbed and its absolute bioavailability has been reported to be around 40%.

Attempts have been made to derivatise EPO to improve its pharmacokinetic properties. There is a product under development by Roche, known as CERA (Constant Erythropoiesis Receptor Activator), which is a polyethyleneglycol derivatised form of EPO. This has been shown to have a longer half-life than EPO, reducing the necessity of frequent injections. A further novel erythropoiesis stimulating agent is Hematide, a novel, PEGylated, synthetic peptide for the treatment of anaemia associated with chronic kidney disease and cancer. This is described further by Fan et al (2006).

Other forms of EPO have also been developed, such as Darbepoetin, a hyperglycosylated analogue of recombinant human erythropoietin which has around a three-fold longer terminal half life after i.v. administration than recombinant human EPO and the native hormone.

EP 1219636 describes modified muteins of EPO produced from a microorganism with a prolonged plasma half-life in the circulation. A cell-free protein synthesis technique is used to produce a mutein of EPO with an unnatural amino acid which may be reacted with a modifier such as PEG or a polysaccharide. Generally, PEG is attached to a free sulfhydryl group in the muteins of EPO.

U.S. Pat. No. 7,128,913 is directed to N-terminal conjugates of EPO with PEG. The conjugates have an increased circulating half life and plasma residence time.

US 2004/0082765 describes an improved method for generating PEG-conjugated EPO. The inventors found that a composition of conjugates having 1-3 linear PEG molecules per rhEPO molecule provided the most sustained efficacy.

U.S. Pat. No. 7,074,755 also addresses the problem of providing improved biologically active EPO conjugate compositions. The EPO is covalently conjugated to a non-antigenic hydrophilic polymer covalently linked to an organic molecule that increases the circulating serum half-life of the composition. The water-soluble polymer may be a polyalkylene oxide, a polyamide, or a carbohydrate, amongst others.

However, there has been no published work to date describing the derivatisation of EPO with anionic polysaccharides such as polysialic acid (PSA).

Polysialic acids (PSAs) are naturally occurring unbranched polymers of sialic acid produced by certain bacterial strains and in mammals in certain cells. They can be produced in various degrees of polymerisation from n=about 80 or more sialic acid residues down to n=2 by limited acid hydrolysis or by digestion with neuraminidases, or by fractionation of the natural, bacterially derived forms of the polymer.

In recent years, the biological properties of polysialic acids, particularly those of the alpha-2,8 linked homopolymeric polysialic acid, have been exploited to modify the pharmacokinetic properties of protein and low molecular weight drug molecules. Polysialic acid derivatisation gives rise to dramatic improvements in circulating half-life for a number of therapeutic proteins including catalase and asparaginase, and also allows such proteins to be used in the face of pre-existing antibodies raised as an undesirable (and sometimes inevitable) consequence of prior exposure to the therapeutic protein. The alpha-2,8 linked polysialic acid offers an attractive alternative to PEG, being an immunologically invisible biodegradable polymer which is naturally part of the human body, and which degrades, via tissue neuraminidases, to sialic acid, a non-toxic saccharide.

We have previously described methods for the attachment of polysaccharides (in particular PSA) to therapeutic agents such as proteins [U.S. Pat. No. 5,846,951; WO-A-0187922]. Some of these methods depend upon chemical derivatisation of the 'non-reducing' end of the polymer to create a protein-reactive aldehyde moiety which reacts at primary amine groups. A non-reducing sialic acid terminal unit, since it contains vicinal diols, can be readily (and selectively) oxidised with periodate to yield a mono-aldehyde form, which is much more reactive towards proteins, and which comprises a suitably reactive element for the attachment of proteins via reductive amination and other chemistries. The reaction is illustrated in FIGS. 1 and 2 wherein;

FIG. 1 shows the oxidation of colominic acid (alpha-2,8 linked polysialic acid from *E. coli*) with sodium periodate to form a protein-reactive aldehyde at the non-reducing end; and FIG. 2 shows the selective reduction of the Schiff's base with sodium cyanoborohydride to form a stable irreversible covalent bond with the protein amino group.

Unintentional by-products may be generated during the conventional conjugation reactions described above by reaction of the colominic acid with side chains of amino acids, for instance. These may be sufficient to be troublesome in the manufacture of chemically defined conjugates required by regulatory authorities for therapeutic use in man and animals.

It is not straightforward to purify the intended reaction product (for instance the monopolysialylated product) away from the various unintended products, since the physicochemical characteristics of most of the reaction products are similar. This means that techniques such as ion-exchange chromatography and gel-permeation chromatography (which separate on the basis of charge and size respectively) produce poor purification profiles. This problem can be overcome by reducing the product complexity in the conjugation reaction. We have developed a new method for conjugation of polysaccharides to proteins whereby the high reactivity of the N-terminal of the protein can be utilised and which avoids the product complexity obtained using the established method (FIGS. 1 and 2) of reductive amination of proteins with periodate oxidised natural colominic acid.

In view of the prior art, there is a need to provide improved derivatives of EPO which can be used in human and animal therapy and have optimised stability, half lives and low toxicity. We have found that attaching polysaccharides such as PSAs to EPO imparts such properties and have thereby arrived at this invention. This is the first time that EPO linked to anionic polysaccharides has been described.

In accordance with a first aspect of this invention we provide a compound which is a polysaccharide derivative of EPO, or of an EPO like protein, wherein the polysaccharide is anionic and comprises between 2 and 200 saccharide units.

Hereinafter, when using the term EPO, we also intend to cover EPO-like proteins. By EPO-like protein, we mean a protein which has an activity equivalent to that of EPO. EPO regulates erythrocyte production, as detailed above. The activity of EPO or an EPO-like protein can be measured using a standard assay as described in Krystal (1983). The activity of EPO samples in inducing proliferation in vitro of erythrocyte progenitor cells isolated from the spleen of a mouse is measured. The mice have previously been rendered anaemic artificially through I.P. injection of phenylhydrazine. In the assay, EPO is added to erythrocyte progenitors and the rate of DNA replication is measured by determining the rate of incorporation of $^3$H-thymidine. A protein is classified as "EPO-like" if it induces 10-200% of the rate of replication compared to standard EPO from NIBSC. Typically, an EPO-like protein has at least 35% of the activity of standard EPO, and preferably, at least 50% of the activity of standard EPO.

Mutants of EPO which have the requisite activity, as detailed above, may also be used. An "EPO-like" protein may also be referred to as an "EPO-homologue". Whether two sequences are homologous is routinely calculated using a percentage similarity or identity, terms that are well known in the art. Sequences should be compared to the human EPO precursor with swissprot accession number P01588. The active EPO is residues 28-193 of this sequence. EPO homologue sequences may either be compared to the whole of SEQ I.D. No. 1, or residues 28-193 thereof. Preferably, EPO homologue sequences are compared to the active EPO, i.e. residues 28-193.

In this invention, homologues have 50% or greater similarity or identity at the nucleic acid or amino acid level, preferably 60%, 70%, 80% or greater, more preferably 90% or greater, such as 95% or 99% identity or similarity at the amino acid level. A number of programs are available to calculate similarity or identity; preferred programs are the BLASTn, BLASTp and BLASTx programs, run with default parameters (available on the NCBI-NIH database). For example, 2 amino acid sequences may be compared using the BLASTn program with default parameters (score=100, word length=11, expectation value=11, low complexity filtering=on). The above levels of homology may be calculated using these default parameters.

The EPO may be glycosylated or non-glycosylated. When the EPO is glycosylated, the compound typically comprises 2-100 saccharide units. More typically, the compound comprises 10-80 saccharide units, preferably 20-60 saccharide units, most preferably 40-50 saccharide units.

When the EPO is non-glycosylated, the compound typically comprises 80-180 saccharide units, preferably 100-150 saccharide units, more preferably 120-145, most preferably 130-140 units.

Preferably, the anionic polysaccharide has at least 2, more preferably at least 5, most preferably at least 10, for instance at least 50 saccharide units.

The anionic polysaccharide is preferably selected from polysialic acid, heparin, hyaluronic acid and chondroitin sulphate. Preferably, the polysaccharide is polysialic acid and consists substantially only of sialic acid units. However, the polysaccharide may have units other than sialic acid in the molecule. For instance, sialic acid units may alternate with other saccharide units. Preferably, however, the polysaccharide consists substantially of units of sialic acid.

Preferably, the compound is an N-terminal derivative of EPO or of an EPO-like protein, that is, the polysaccharide is associated with the EPO at its N-terminus. In this specification, by derivatisation at the N-terminus, we mean derivatisation at the N-terminal amine group of the EPO. Alternatively, however, the polysaccharide may be associated with the EPO or EPO-like protein at a mid-chain amino acid, such as at the side chain of a lysine, cysteine, aspartic acid, arginine, glutamine, tyrosine, glutamic acid or histidine. Typically, the side chain is of a lysine or cysteine amino acid.

Preferably the polysaccharide has a terminal sialic acid group, and as detailed above, is more preferably a polysialic acid, that is a polysaccharide comprising at least 2 sialic acid units joined to one another through α-2-8 or α-2-9 linkages. A suitable polysialic acid has a weight average molecular weight in the range 2 to 50 kDa, preferably in the range 5 to 50 kDa. Most preferably, the polysialic acid is derived from a bacterial source, for instance polysaccharide B of *E. coli* KI, *N. meningitidis*, *Maraxella liquefaciens* or *Pasteurella aeruginosa* or K92 polysaccharide from *E. coli* K92 strain. It is most preferably colominic acid from *E. coli* K1.

The polysialic acid may be in the form of a salt or the free acid. It may be in a hydrolysed form, such that the molecular weight has been reduced following recovery from a bacterial source.

The polysaccharide, which is preferably polysialic acid may be material having a wide spread of molecular weights such as having a polydispersity of more than 1.3, for instance as much as 2 or more. Preferably the polydispersity (p.d.) of molecular weight is less than 1.3, more preferably less than 1.2, for instance less than 1.1. The p.d. may be as low as 1.01.

The EPO may be derivatised with more than one anionic polysaccharide. For instance, the EPO may be derivatised at both its N-terminus and at an internal amino acid side chain. The side chains of lysine, cysteine, aspartic acid, arginine, glutamine, tyrosine, glutamic acid, serine and histidine, for instance, may be derivatised by an anionic polysaccharide. The EPO may also be derivatised on a glycon unit. However, in a preferred embodiment of this invention, the EPO is derivatised at its N-terminus only.

In this specification, by derivatisation at the N-terminus, we mean derivatisation at the N-terminal amine group of the EPO.

The compound according to the first aspect of this invention may be a covalently-linked conjugate between the EPO and an anionic polysaccharide. Other means of association between the polysaccharide and the EPO include electrostatic attraction. However, covalent bonding is preferred. The EPO may be covalently linked to the polysaccharide at its N-terminal amino acid. The covalent linkage may be an amide linkage between a carboxyl group and an amine group. Another linkage by which the EPO could be covalently bonded to the polysaccharide is via a Schiff base. Suitable groups for conjugating to amines are described further in WO2006/016168.

In the invention the polysaccharide may be a naturally occurring polysaccharide, or a derivative of a naturally occurring polysaccharide, for instance, a polysaccharide which has been derivatised by a reaction of one or more active groups on the saccharide residues, or which has been covalently linked to a derivatising group at the end of the polysaccharide chain.

The polysaccharide may be linked to the EPO via either its reducing or non-reducing terminal unit. This means that one polysaccharide chain may be linked to two EPO proteins, i.e. be derivatised at both its reducing and non-reducing end.

Methods for attaching polysaccharides to proteins are well known in the art and are described in more detail in WO92/22331 and WO-A-0187922. The preferred methods in this invention are described in more detail below. Methods are also described in FIGS. 1 and 2 of this Application.

The polysaccharide may be linked to the EPO or EPO-like protein directly, i.e. as shown in FIGS. 1 and 2, or via a linker. Suitable linkers are derived from N-maleimide, vinylsulphone, N-iodoacetamide, orthopyridyl or N-hydroxysuccinimide-containing reagents. The linker may also be biostable or biodegradable and comprise, for instance, a polypeptide or a synthetic oligomer. The linker may be derived from a bifunctional moiety, as further described in WO2005/016973. A suitable bifunctional reagent is, for instance, Bis-NHS. The reagent may have general formula Z—R$^1$—Z wherein each Z is a functional group and may be the same or different and R$^1$ is a bifunctional organic radical. Preferably, R$^1$ is selected from the group consisting of alkanediyl, arylene, alkarylene, heteroarylene and alkylheteroarylene, any of which may substituted and/or interrupted by carbonyl, ester, sulfide, ether, amide and/or amine linkages. Particularly preferred is $C_3$-$C_6$ alkanediyl. Most preferably, R$^1$ corresponds to the appropriate portion of the suitable bifunctional reagent.

A preferred compound of this invention is of general formula (I)

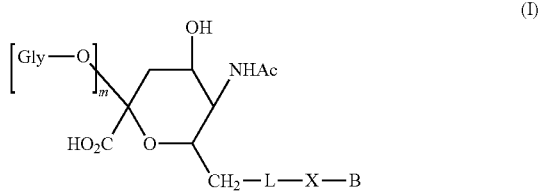

wherein m is at least one;
XB is derived from B—XH which is EPO or an EPO-like protein wherein XH is $NH_2$ or SH;
L is a bond, a linking group, or comprises a polypeptide or a synthetic oligomer;
GlyO is an anionic saccharide unit;
wherein the linking group, if present, is of general formula —Y—C(O)—R$^1$—C(O)—; wherein Y is NR$^2$ or NR$^2$—NR$^2$ and R$^1$ is a bifunctional organic radical as defined above; and R$^2$ is H or $C_{1-6}$ alkyl.

In this aspect of the invention the EPO is linked to the non-reducing end of the polysaccharide. The terminal polysaccharide unit is a sialic acid unit. The other saccharide units in the polysaccharide are represented by GlyO and may be the same or different. Suitable saccharide units include heparin, hyaluronic acid and chondroitin sulphate.

When the EPO is attached directly to the polysaccharide, the group L is a bond. However, the group L may alternatively be derived from an N-maleimide, vinylsulphone, N-iodoacetamide, orthopyridyl or N-hydroxysuccinimide containing reagent. The reagent may have general formula Z—R$^1$—Z as defined above. In this embodiment, L is typically a group

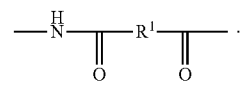

Preferably, XH is $NH_2$ and is the N-terminus of the EPO or EPO-like protein. Alternatively, $NH_2$ may be the primary amine of a lysine amino acid side chain. In a different embodiment, XH is a thiol group, SH, of the side chain of a cysteine amino acid.

Another aspect of the invention is a pharmaceutical composition comprising a novel compound as defined above and one or more pharmaceutically acceptable excipients.

The pharmaceutical composition may be in the form of an aqueous suspension. Aqueous suspensions contain the novel compounds in admixture with excipients suitable for the manufacture of aqueous suspensions. The pharmaceutical compositions may be in the form of a sterile injectable aqueous or homogeneous suspension. This suspension may be formulated according to the known art using suitable dispersing or wetting agents and suspending agents.

Pharmaceutical compositions may be administered orally, intravenously, intraperitoneally, intramuscularly, subcutaneously, intranasally, intradermally, topically or intratracheally for human or veterinary use.

The compositions may further comprise a formulation additive. By formulation additive we mean an excipient which is capable of stabilising the EPO either internally or externally, as described in Wang et al (1999). The excipient may be a stabiliser, a solubilser or a metal ion. Suitable examples of formulation additives include one or more buffers, stabilisers, surfactants, salts, polymers, metal ions, sugars, polyols or amino acids. These may be used alone or in combination.

Stabilisers typically act by destabilisation of the denatured state of a protein leading to increased Gibbs free energy change for unfolding of the protein. The stabiliser is preferably a sugar or a polyol, for example sucrose, sorbitol, trehalose, glycerol, mannitol, lactose and ethylene glycol. A stabilising buffer is sodium phosphate.

The solubiliser is preferably a surfactant, preferably a non-ionic surfactant. Suitable examples include Tween 80, Tween 20, Tween 40, Pluoronic F68, Brij 35 and Triton X100.

The metal ion is preferably divalent. Suitable metal ions include $Zn^{2+}$, $Ni^{2+}$, $Co^{2+}$, $Sr^{2+}$, $Cu^{2+}$ and $Fe^{2+}$.

The formulation additive may also be a polymer selected from human serum albumin, PSA, PEG or hydroxy-beta-cyclodextrin.

Suitable amino acids and amino acid derivatives for use as the formulation additive include histidine, glycine, other similar amino acids and sodium aspartate.

Another aspect of this invention is a composition comprising a population of anionic polysaccharide derivatives of EPO or an EPO-like protein, wherein the derivatives comprise between 2 and 125 saccharide units and wherein the population consists of substantially only N-terminal derivatives of the protein. By "population" we mean that there is more than one polysaccharide derivative in the composition. The derivatives may comprise the same or different numbers of saccharide units. Preferably, the polydispersity of the polysaccharide in the composition is less than 1.3, more preferably less than 1.1. Preferred polysaccharides are as detailed above for the other aspects of this invention.

In the population, substantially all of the EPO is derivatised at the N-terminus only. By this, we mean that 85%, preferably at least 90%, most preferably at least 95% of the protein in the population is derivatised with PSA at the N-terminus only.

The degree of derivatisation at the N-terminus may be determined by techniques known in the art such as peptide mapping or Edman Degradation.

A further aspect of the invention is a compound as described above for use in therapy.

In accordance with a final aspect of the invention, we provide a method for producing a polysaccharide derivative of EPO or of an EPO-like protein wherein an anionic polysaccharide comprising 2-200 saccharide units is chemically reacted with the EPO or EPO-like protein.

It will be noted in this aspect of the invention, the polysaccharide may react at any group on the EPO or EPO-like protein. For instance, the polysaccharide may react with an amine, hydroxyl, carboxyl or sulfhydryl group. Preferably, the group is an amine group, more preferably a terminal amine group. The amine may alternatively be the amine side chain of an amino acid, such as a lysine amino acid. The polysaccharide may also react at any carbohydrate residues on the EPO, such as on pendant glycone groups.

Polysaccharides may be linked to amino acid side chains by methods known on the art. For instance, a polysaccharide may be coupled to the C-terminal, —COOH or carboxyl side chains of Asp or Glu by in vitro coupling. Thiol groups of cysteine amino acids may also be linked to polysaccharides by in vitro coupling. These methods are described further in WO03/055526, in particular the table on pages 6 and 7. In this reference, in vitro coupling is also used to link an oligosaccharide moiety to the amide group on the side chain of Gln. In vitro imidazole groups of Arg and His residues respectively are also described. Each of these methods may be used to derivatise the EPO of the present invention.

The polysaccharide may also react with a modified form of EPO. For instance, one or more groups on the EPO may have undergone a chemical transformation, for instance, by reduction or oxidation. A reactive carbonyl may be generated in the place of the terminal amino group of EPO using oxidation conditions, for instance.

Suitable polysaccharides for use in the method of this invention are as described previously for the novel compounds.

The compounds of the invention may be manufactured by any of the suitable methods described in the prior art. For example, a typical method is described to our previous Patent Application WO92/22331.

Typically, the anionic polysaccharide has been activated before derivatisation to EPO. It may, for instance, have a reactive aldehyde group and the derivatisation reaction may be carried out under reducing conditions. The reactive aldehyde group may be produced by controlled oxidation of a hydroxyl group of the polysaccharide. Most preferably this reactive aldehyde is generated in a preliminary step, in which the polysaccharide is reacted under controlled oxidation conditions, for instance using sodium periodate, in aqueous solution. Preferably the oxidation is a chemical oxidation, although enzymes which are capable of carrying out this step may also be used. The reactive aldehyde group may be at the non-reducing end or reducing end of the polysaccharide. The EPO, typically the N-terminus, may then react with the reactive aldehyde group to produce an adduct which, when reduced, produces the N-terminal derivative of EPO.

The activation of the polysaccharide should preferably be carried out under conditions such that there is substantially no mid-chain cleavage of the backbone of the polysaccharide, that is substantially no molecular weight reduction. The oxidant is suitably perrhuthenate, or, preferably, periodate. Oxidation may be carried out with periodate at a concentration in the range 1 mM to 1M, at a pH in the range 3 to 10, a temperature in the range 0 to 60° C. for a time in the range 1 min to 48 hours.

Suitable reducing conditions for the derivatisation reaction may utilise hydrogen with catalysts or, preferably hydrides, such as borohydrides. These may be immobilised such as AMBERLITE™ (strong acid, gel-type cation exchange resin)-supported borohydride. Preferably alkali metal hydrides such as sodium borohydride is used as the reducing agent, at a concentration in the range 1 μM to 0.1M, a pH in the range 5.0 to 10, a temperature in the range 0 to 60° C. and a period in the range 1 min to 48 hours. The reaction conditions are selected such that pendant carboxyl groups on the starting material are not reduced. Other suitable reducing agents are cyanoborohydride under acidic conditions, e.g. polymer supported cyanoborohydride or alkali metal cyanoborohydride, L-ascorbic acid, sodium metabisulphite, L-selectride, triacetoxyborohydride etc.

Other activated derivatives of polysaccharides may have utility in the present invention, including those with pendant functional groups such as NHS, as described in our earlier Patent Application WO06/00540.

In one embodiment, the reactive aldehyde is at the reducing end of the polysaccharide and the non-reducing end has been passivated such that it does not react with pendant groups on the EPO.

The reactivity of the reducing end of colominic acid, though weak towards protein targets, is sufficient to be troublesome in the manufacture of chemically defined conjugates.

Chemistry suitable for preparing a polysaccharide with a reactive aldehyde at the reducing terminal of a polysaccharide is described in our earlier Application WO05/016974. The process involves a preliminary selective oxidation step followed by reduction and then further oxidation to produce a compound with an aldehyde at the reducing terminal and a passivated non-reducing end.

WO2005/016973 describes polysialic acid derivatives that are useful for conjugation to proteins, particularly those which have free sulfhydryl drugs. The polysialic acid compound is reacted with a heterobifunctional reagent to introduce a pendant functional group for site-specific conjugation to sulfhydryl groups. The anionic polysaccharides used in the present invention may also be derivatised with a heterobifunctional reagent in this manner.

The polysaccharide may be derivatised before it reacts with EPO. For instance, the polysaccharide may react with a bifunctional reagent.

The polysaccharide may be subjected to a preliminary reaction step, in which a group selected from a primary amine group, a secondary amine group and a hydrazine is formed on the terminal saccharide, which is preferably sialic acid, followed by a reaction step in which this is reacted with a bifunctional reagent to form a reaction-intermediate, as further described in WO2006/016168. The intermediate may then react with the EPO. The bifunctional reagent may have general formula Z—$R^1$—Z, as defined previously.

We have found that certain reaction conditions promote selective derivatisation at the N-terminal of the EPO. To promote selective reaction at the N-terminal, the derivatisation reaction should be carried out in a first aqueous solution of acidic pH, and the resultant polysaccharide derivative should then be purified in a second aqueous solution of higher pH than the first aqueous solution. Typically the pH of the first aqueous solution is in the range 4.0-6.0 and the pH of the second aqueous solution is in the range of 6.5-9.0, preferably 6.5-8.5 or 6.5-8.0. The low pH of the derivatisation reaction promotes selective derivatisation at the N-terminus of the protein rather than at any mid-chain sites.

Furthermore, we have found that the use of certain formulation additives promotes the formation of a selective, stable, polysaccharide EPO-derivative. The formulation additive may be selected from one or more buffers, stabilisers, surfactants, salts, polymers, metal ions, sugars, polyols or amino acids. These may be added to the reaction medium, or alternatively may be added to the final product composition, as a stabiliser.

In one embodiment of this invention, the formulation additive is sorbitol, trehalose or sucrose. In a different embodiment, the formulation additive is a non-ionic surfactant. The formulation additive may alternatively be a polymer selected from PSA, PEG or hydroxy-beta-cyclodextrin. In a different embodiment the formulation additive is a divalent metal ion. Preferred divalent metal ions include $Zn^{2+}$, $Ni^{2+}$, $Co^{2+}$, $Sr^{2+}$, $Fe^{2+}$, $Mg^{2+}$ or $Ca^{2+}$.

The formulation additive may be a buffer. Preferably when the formulation additive is a buffer, it is sodium phosphate.

The purification of the polysaccharide derivative in the method of the present invention may be carried out using a variety of methods known in the art. Examples of suitable purification methods include HIC (hydrophobic interaction chromatography), SEC (size exclusion chromatography), HPLC (high performance liquid chromatography), AEC (anion exchange chromatography) and metal affinity chromatography.

A population of polysialic acids having a wide molecular weight distribution may be fractionated into fractions with lower polydispersities, i.e. into fractions with differing average molecular weights. Fractionation is preferably performed by anion exchange chromatography, using for elution a suitable basic buffer, as described in our earlier Patent Applications WO2005/016794 and WO2005/03149. The fractionation method is suitable for a polysaccharide starting material as well as to the derivatives. The technique may thus be applied before or after the essential process steps of this invention. Preferably, the resultant polysaccharide derivative of EPO has a polydispersity of less than 1.3, more preferably less than 1.2, most preferably less than 1.1.

The derivatisation of EPO in accordance with this invention, results in increased half-life, improved stability, reduced immunogenicity, and/or control of solubility of the protein. Hence the bioavailability and the pharmacokinetic properties of EPO are improved. The new method is of particular value for creation of a monopolysialylated-EPO conjugate.

The invention is illustrated by Examples 1 to 3.12 and by reference to the following drawings:—

Figure 7:
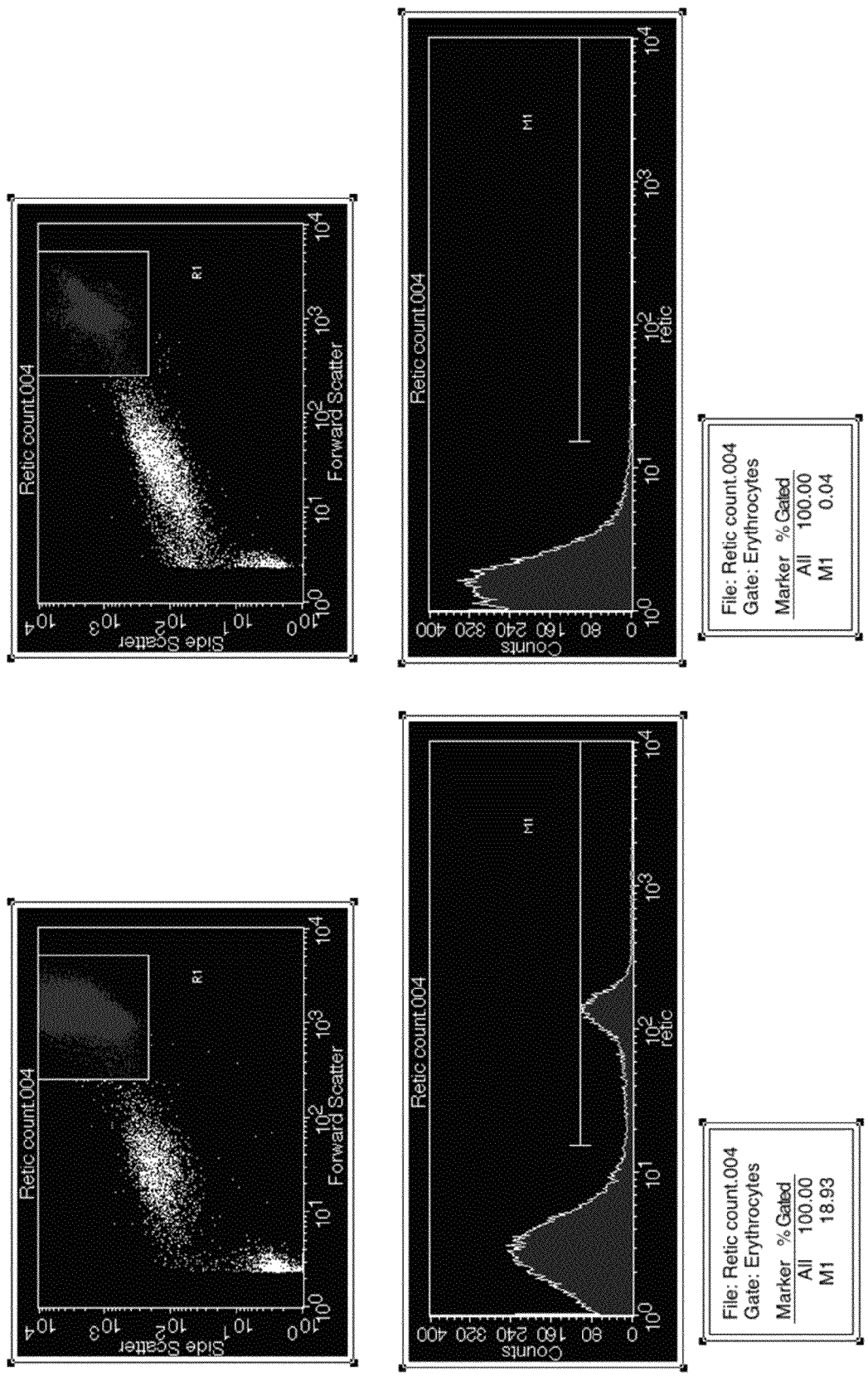
Figure 8:
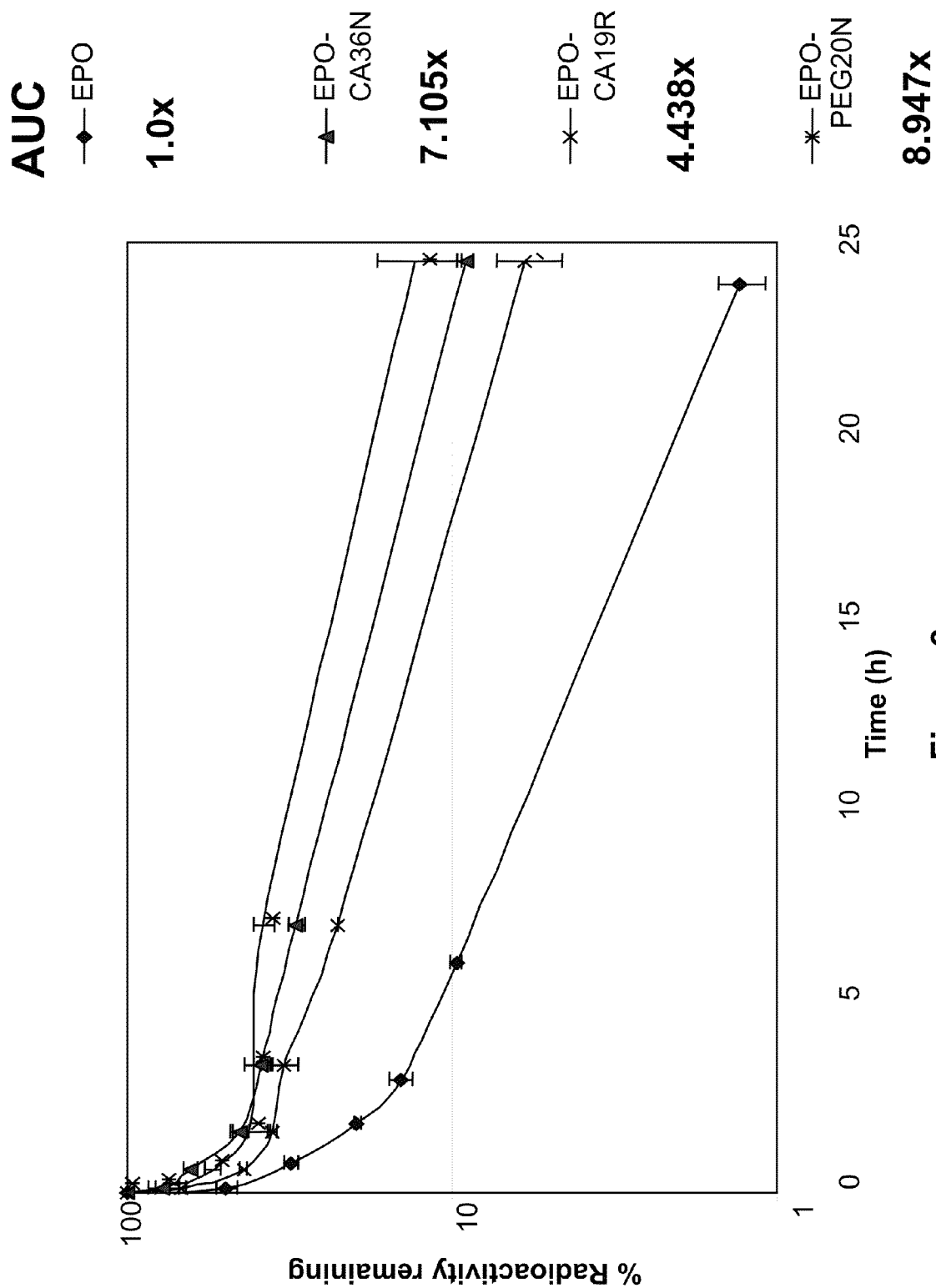
Figure 9:
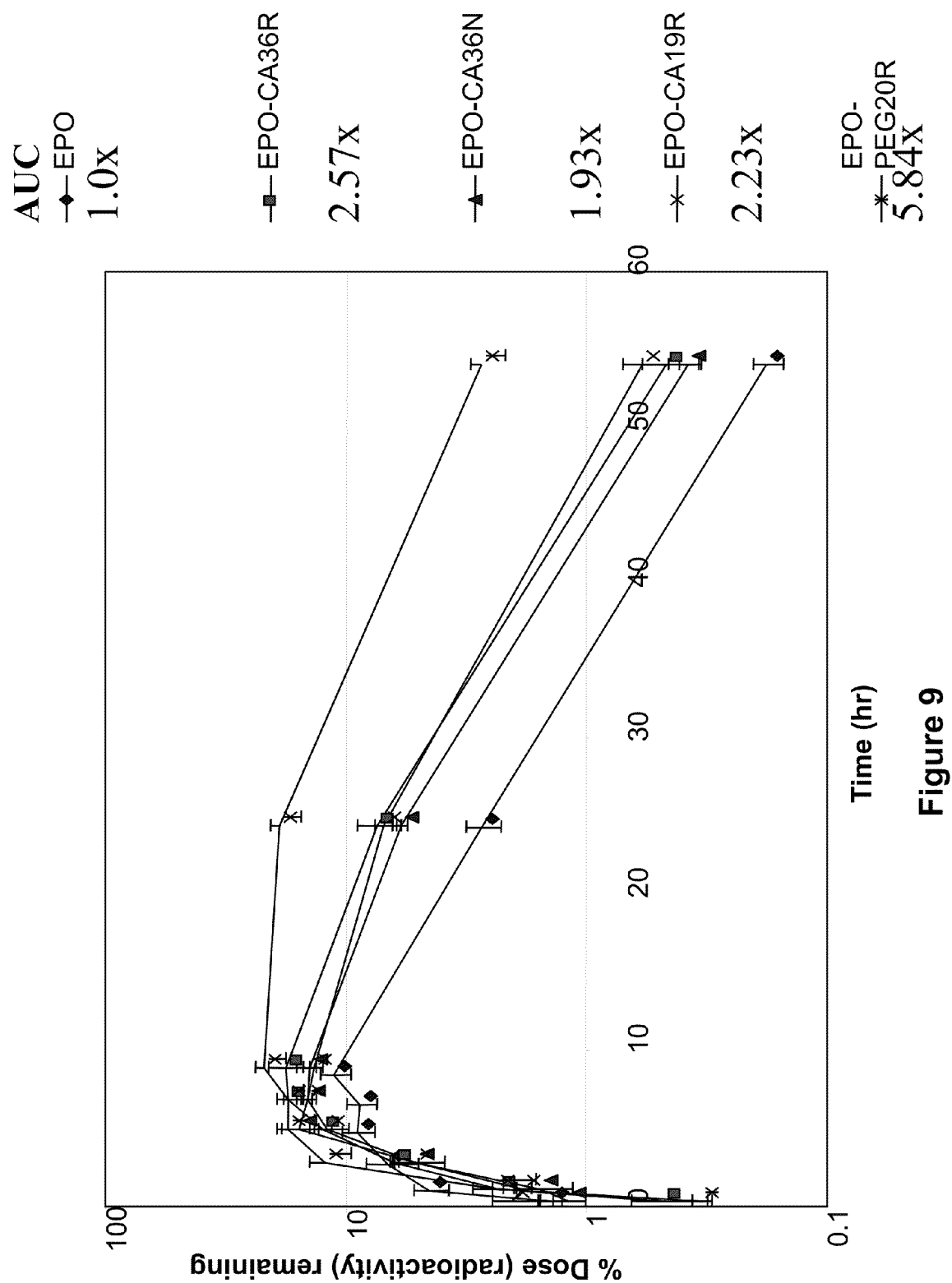
Figure 10:
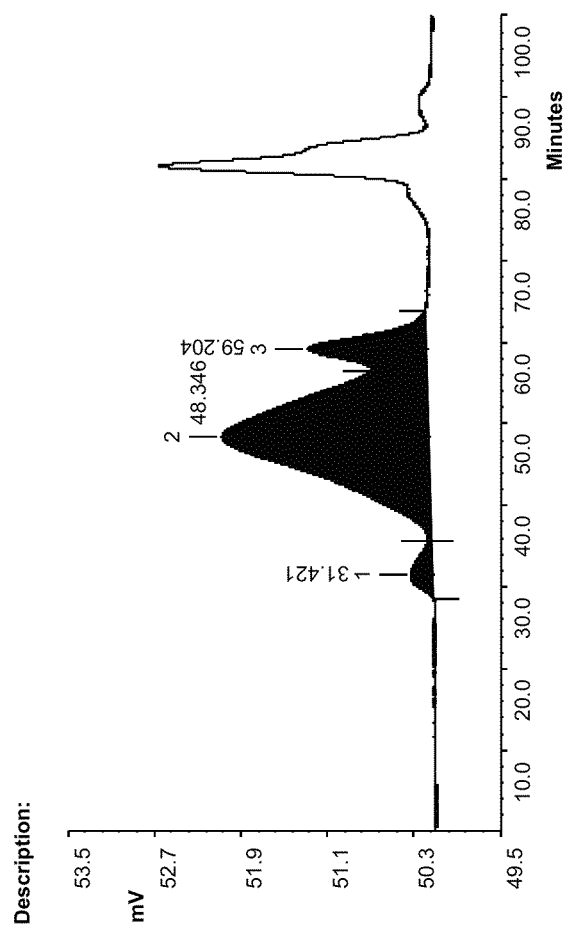
Figure 11:
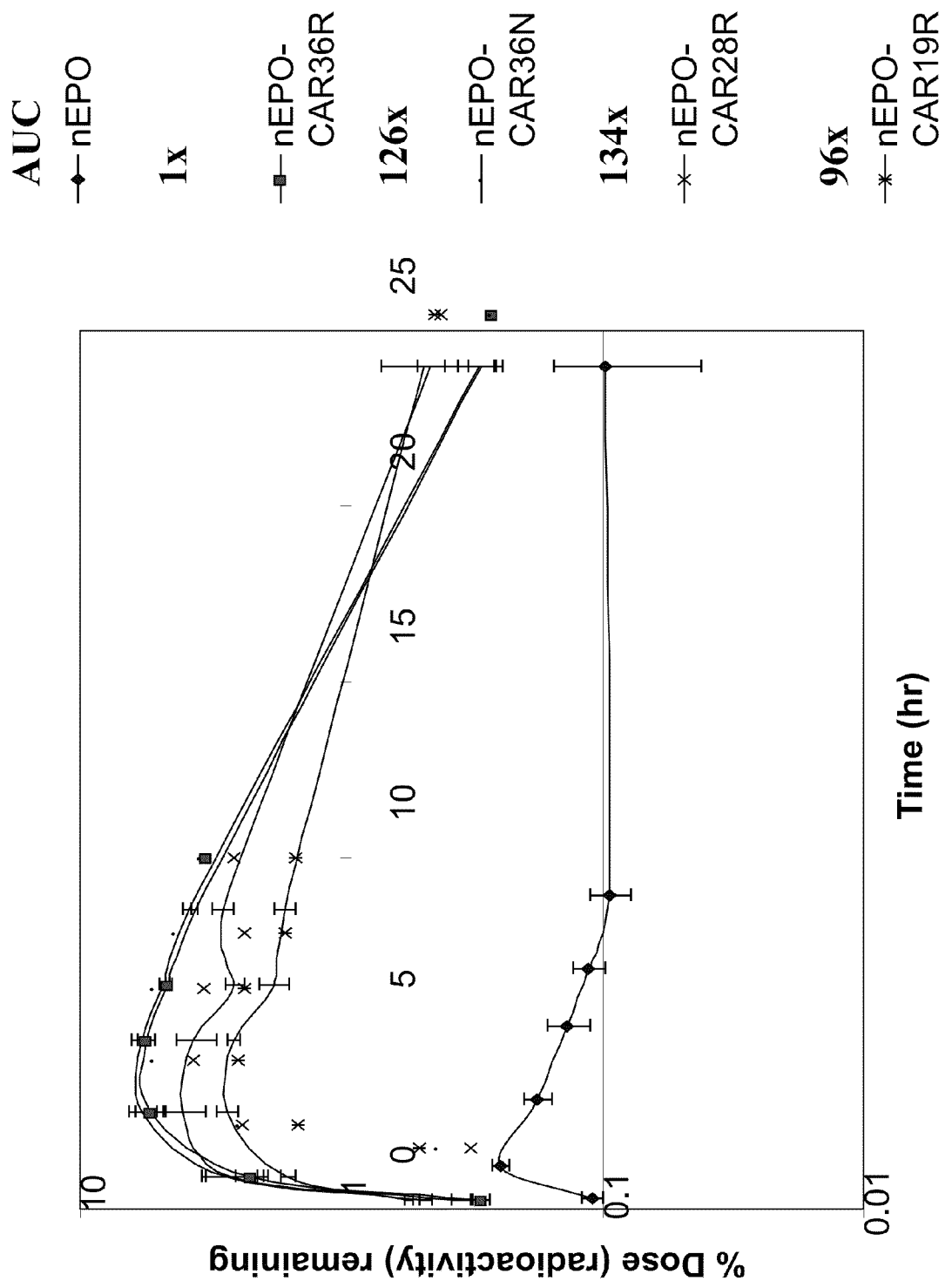
Figure 12:
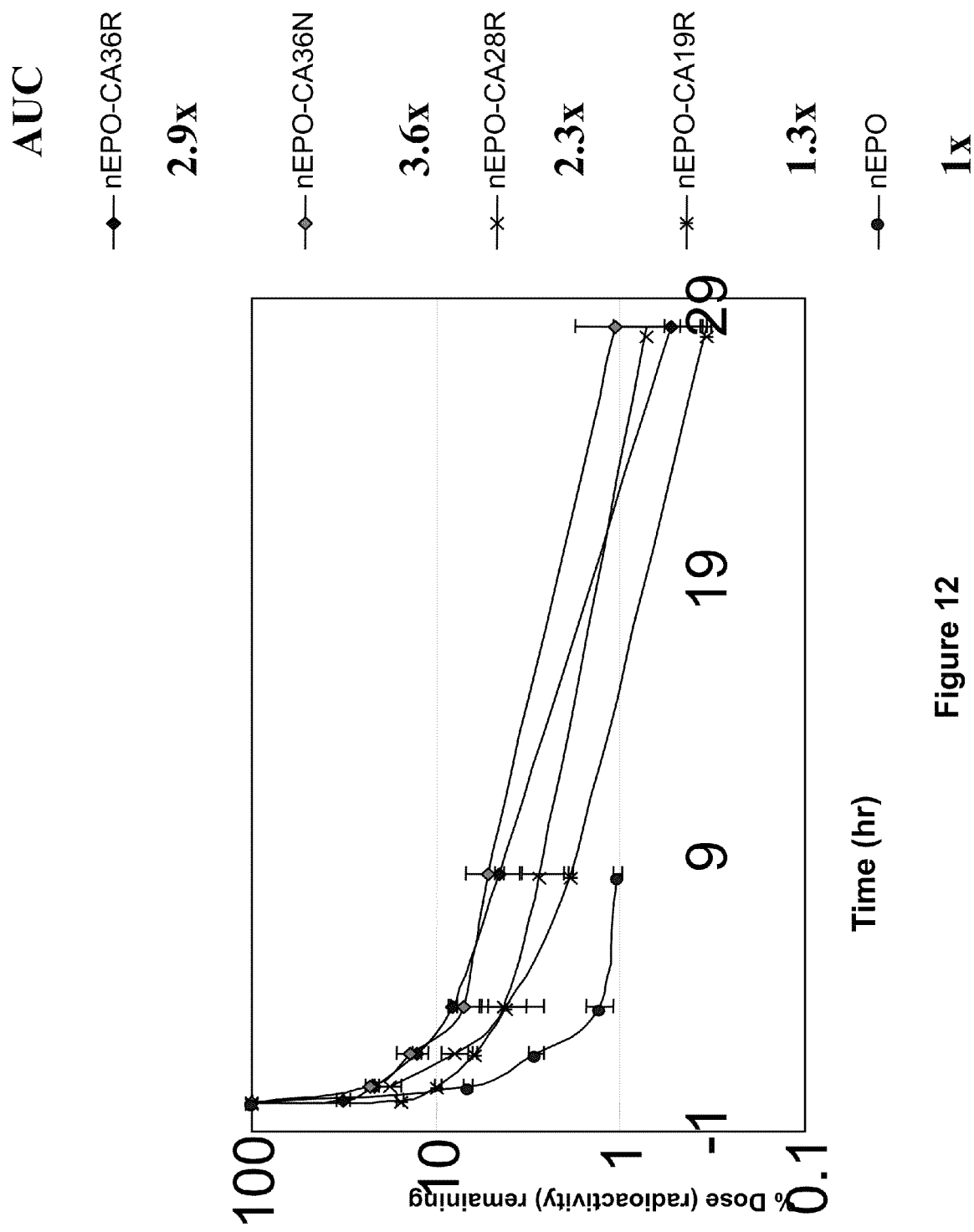
Figure 13:
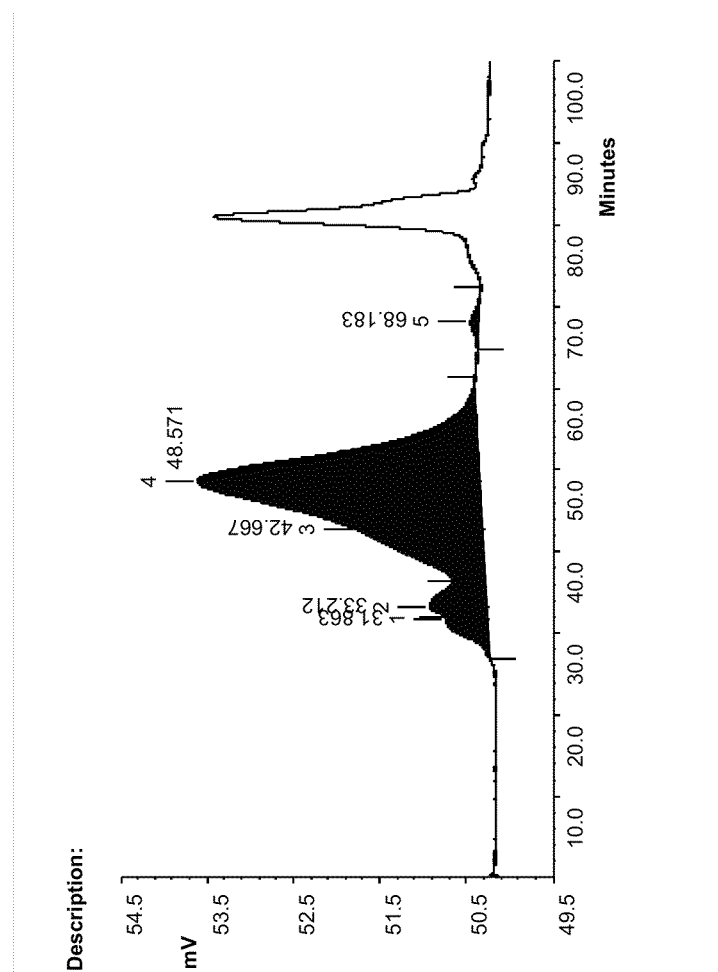
Figure 14:
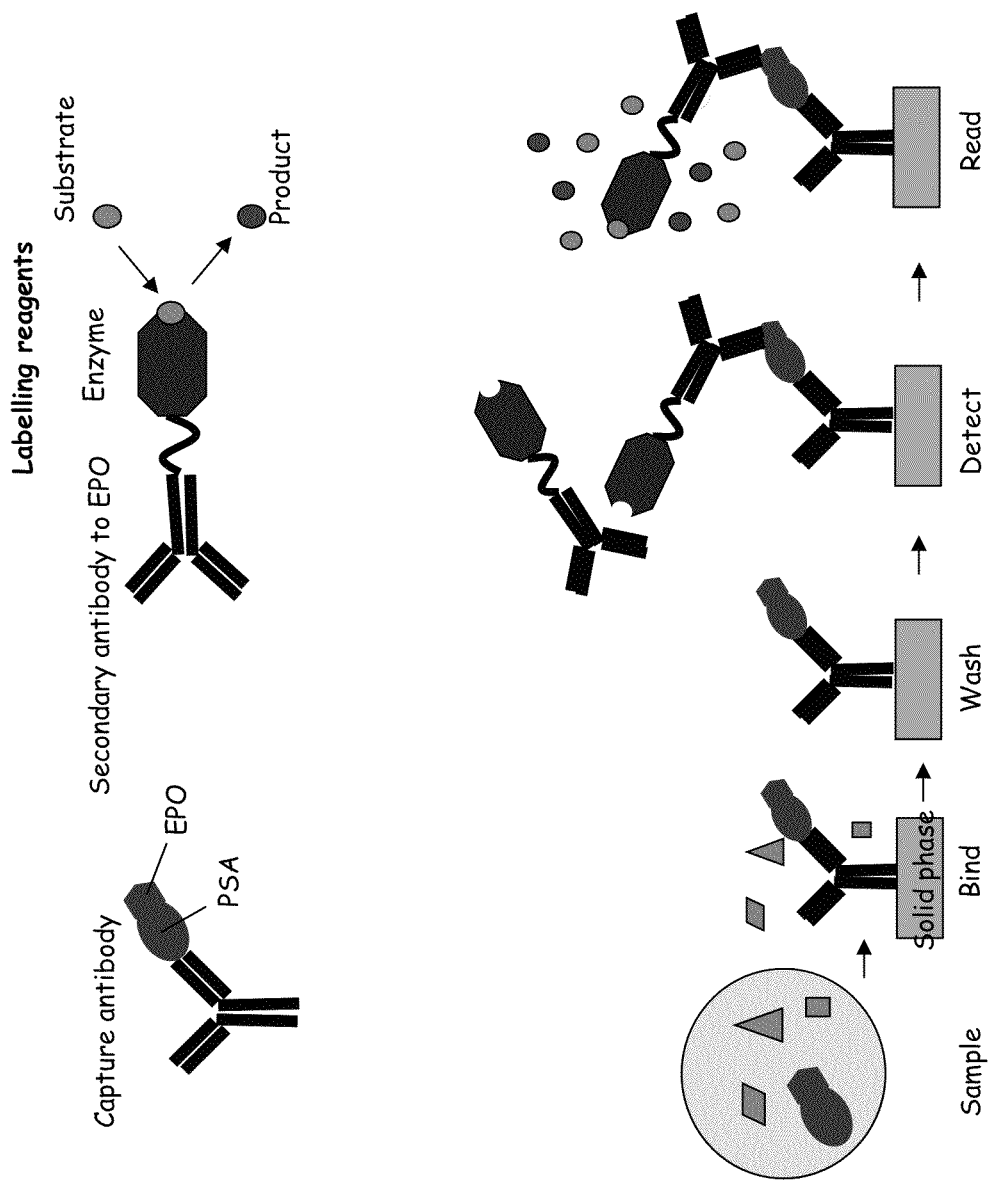
Figure 15:
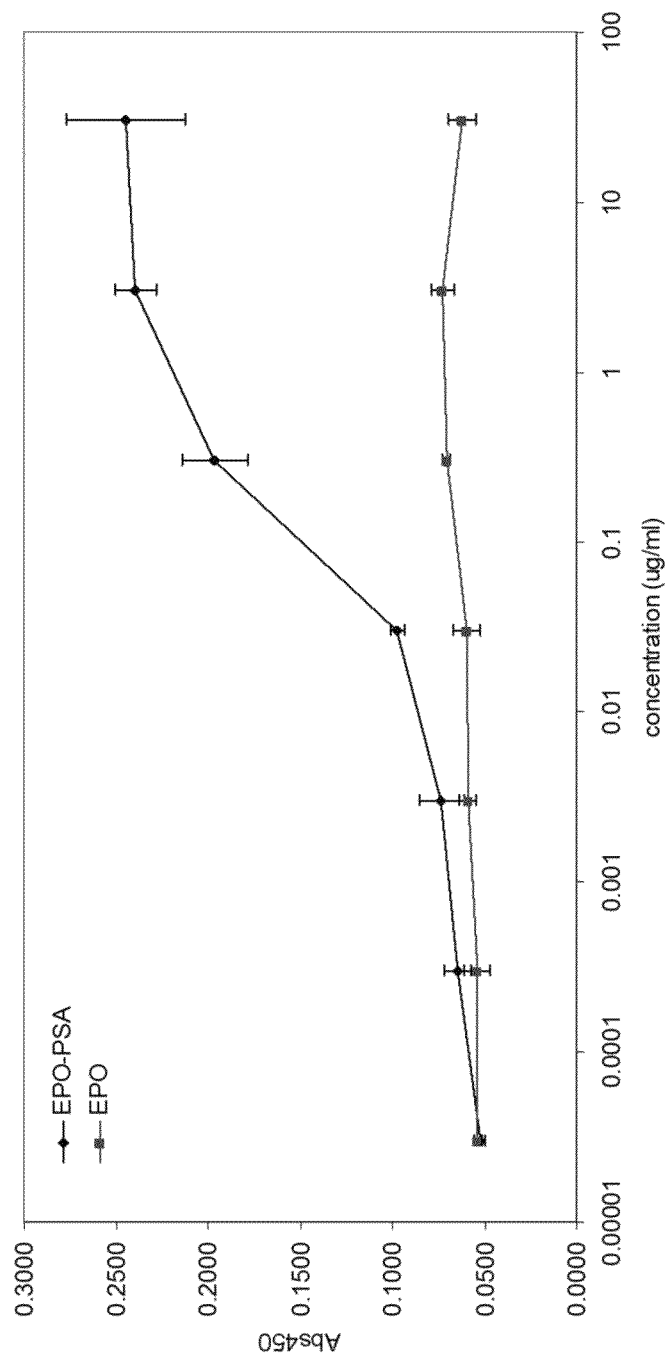
Figure 16:
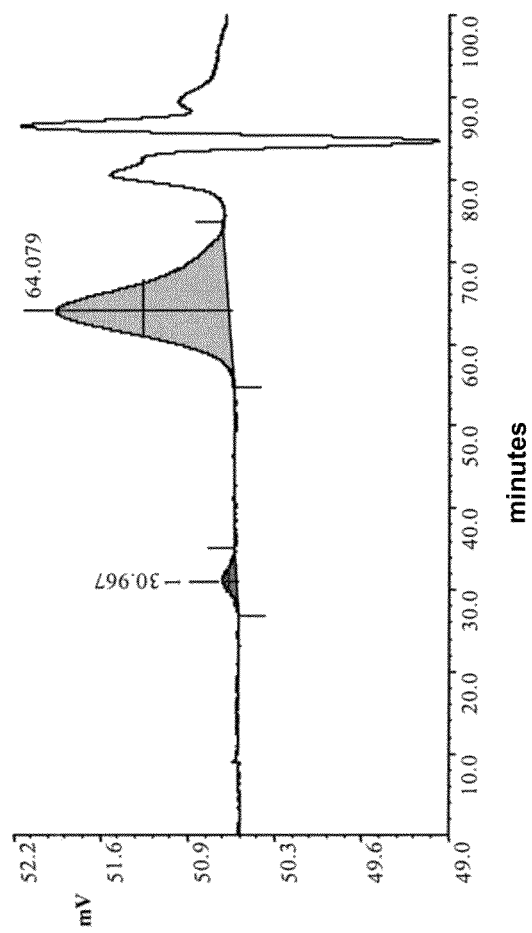
Figure 17:
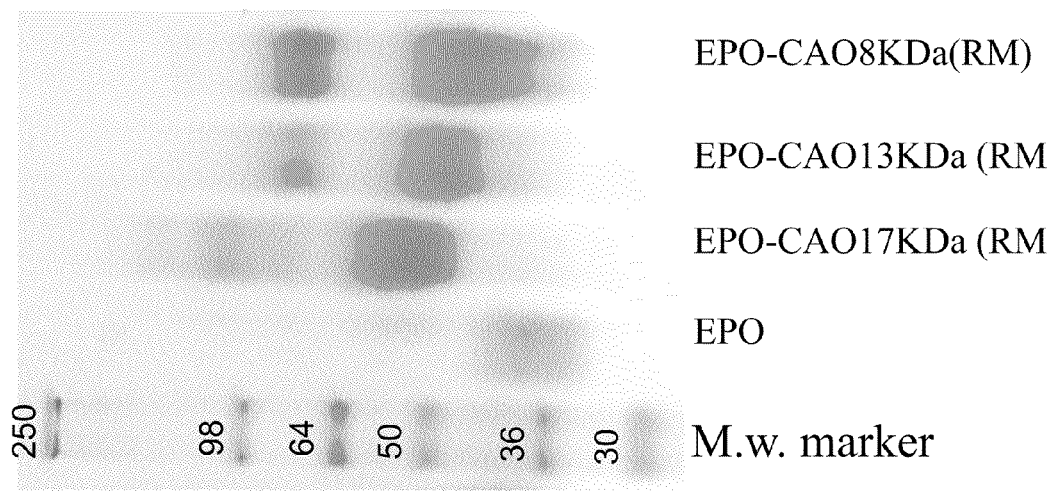
Figure 18:
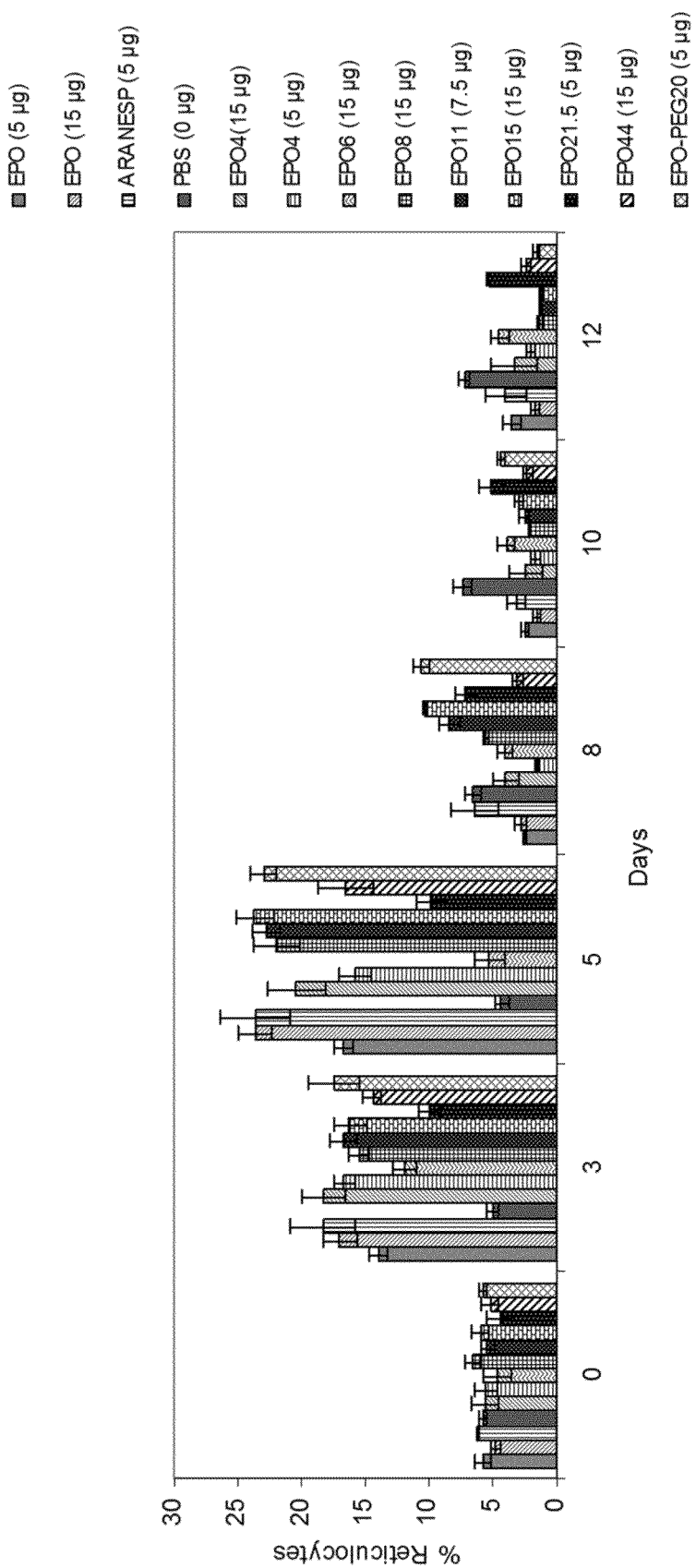
Figure 19:
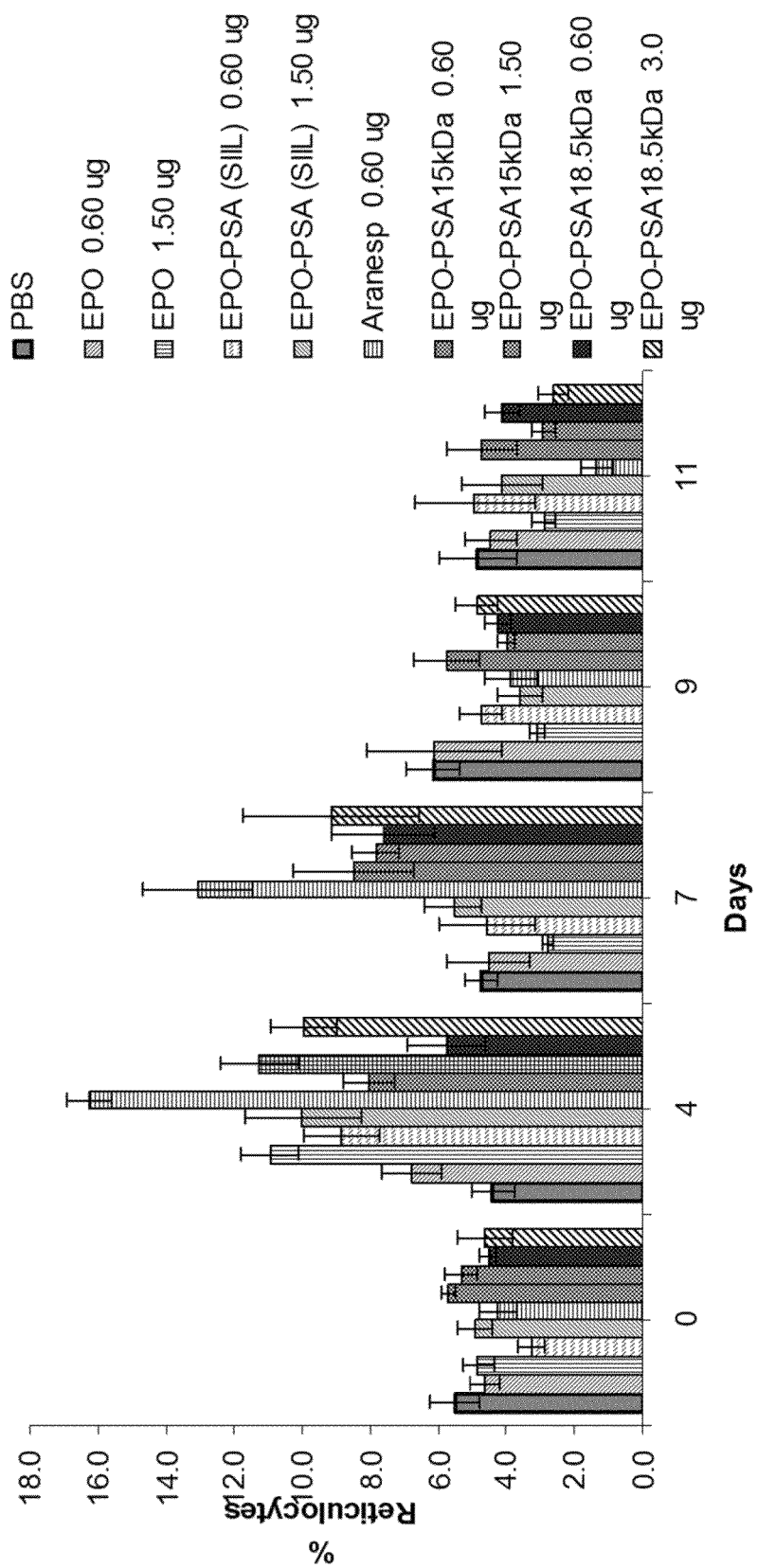
Figure 20:
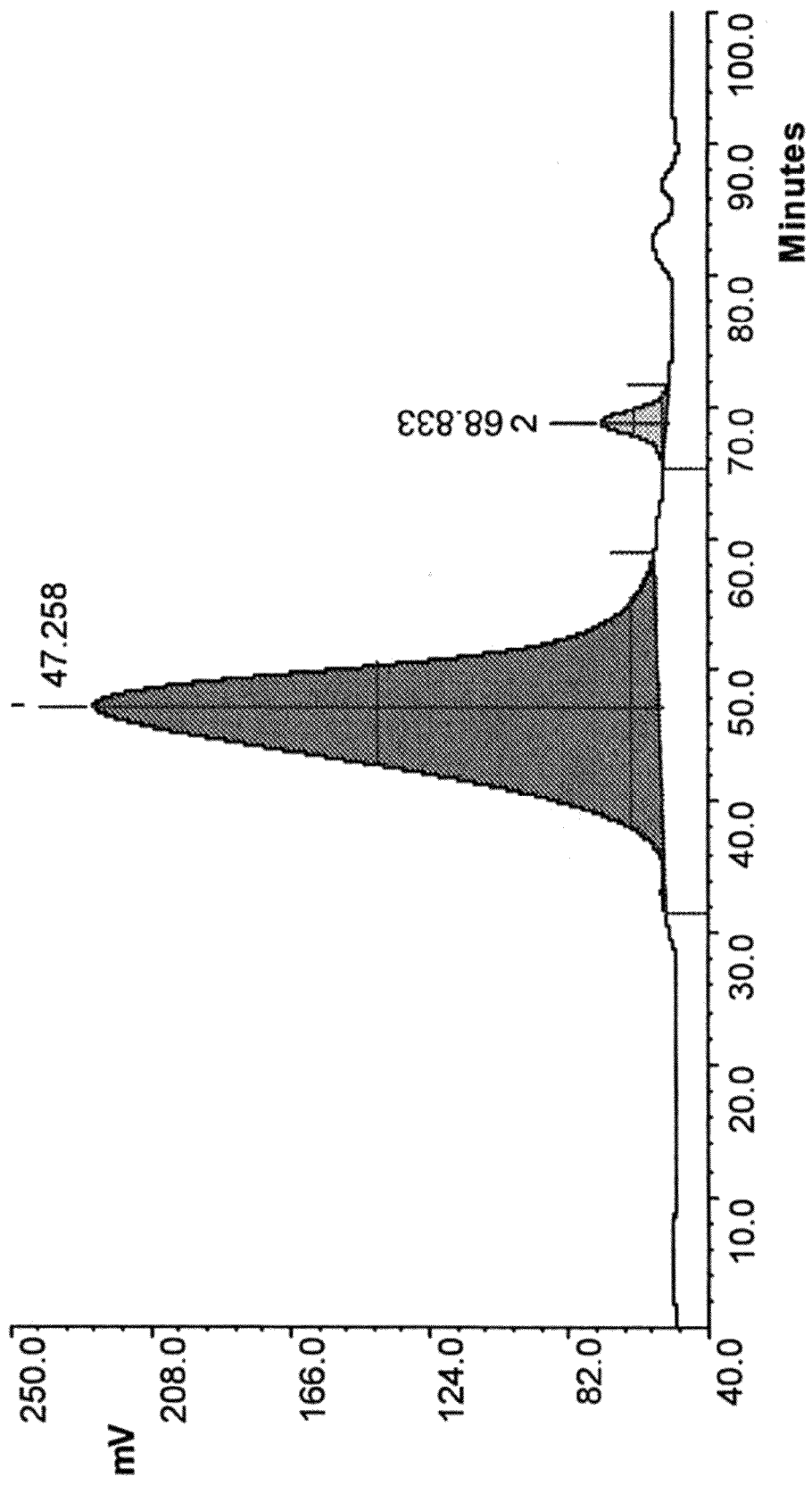

FIGS. 6a-d show the characterisation of EPO, polysialylated and PEGylated EPO by SE-HPLC;

FIG. 7 shows the FACS data for EPO (reticulocytes count);

FIG. 8 shows in vivo clearance of EPO formulations;

FIG. 9 shows in vivo clearance of EPO formulations;

FIG. 10 shows characterization of EPO-CA conjugates by SE-HPLC;

FIG. 11 shows in vivo clearance of non glycosylated EPO vs. polysialylated non glycosylated EPO;

FIG. 12 shows in vivo clearance of non glycosylated EPO vs. polysialylated non glycosylated EPO;

FIG. 13 shows characterisation of NG-EPO-CA conjugates by SE-HPLC and SDS PAGE;

FIG. 14 shows detection of EPO PSA by sandwich ELISA;

FIG. 15 shows sensitivity of ELISA to EPO-PSA in reagent diluent;

FIG. 16 shows stability of EPO conjugates by size exclusion HPLC;

FIG. 17 shows SDS-PAGE of polysialylated EPO;

FIG. 18 shows in vivo efficacy of EPO formulations (n=3-4±SE) to outbred female mice; 12 weeks old; SC (aldehyde chemistry);

FIG. 19 in vivo efficacy of EPO formulations (Female Wistar rats; 8-9 weeks old; n=5±SEM); and FIG. 20 shows PEGylation of NG EPO by SE-HPLC.

EXAMPLES

Materials

Ammonium carbonate, ethylene glycol, polyethylene glycol (8KDa), sodium cyanoborohydride (>98% pure), sodium meta-periodate and molecular weight markers, ammonium sulphate, sodium chloride, sodium phosphate, sorbitol, Tween 20 and Tris were obtained from Sigma Chemical Laboratory, UK. Sodium acetate and sodium phosphate were from BDH, UK. The colominic acid used, linear alpha-(2,8)-linked *E. coli* K1 polysialic acids (22.7 kDa average, high polydispersity 1.34, 39 kDa p.d. 1.4; 11 kDa, p.d. 1.27) was from Camida, Ireland and S.I.I.L. India Ltd. Other materials included 2,4 dinitrophenyl hydrazine (Aldrich Chemical Company, UK), dialysis tubing (3.5KDa and 10KDa cut off limits; Medicell International Limited, UK), Sepharose SP HiTrap, PD-10 columns, Q FF [column 1 ml or 5 ml]; Hitrap Butyl HP column [1 or 5 ml]; (Pharmacia, UK), Tris-glycine polyacrylamide gels (4-20% and 8-16%), Tris-glycine sodium dodecylsulphate running buffer and loading buffer (Novex, UK). Deionised water was obtained from an Elgastat Option 4 water purification unit (Elga Limited, UK). All reagents used were of analytical grade. A plate reader (Dynex Technologies, UK) was used for spectrophotometric determinations in protein or CA assays. Mice and rats were purchased from Harlan, UK and acclimatised for at least one week prior to their use. EPO was obtained from SIIL, India, 1. Protein and Colominic Acid Determination Quantitative estimation of polysialic acids (as sialic acid) with the resorcinol reagent was carried out by the resorcinol method [Svennerholm, 1957] as described elsewhere [Gregoriadis et al., 1993; Fernandes and Gregoriadis, 1996, 1997]. Protein was measured by the BCA colorimetric method or UV absorbance at 280 nm.

2.1. Activation of Colominic Acid

Freshly prepared 0.02 M sodium metaperiodate ($NaIO_4$) solution (8 fold molar excess) was mixed with CA at 20° C.

and the reaction mixture was stirred magnetically for 15 min in the dark. A two-fold volume of ethylene glycol was then added to the reaction mixture to expend excess $NaIO_4$ and the mixture left to stir at 20° C. for a further 30 min. The oxidised colominic acid was dialysed (3.5KDa molecular weight cut off dialysis tubing) extensively (24 h) against a 0.01% ammonium carbonate buffer (pH 7.4) at 4° C. Ultrafiltration (over molecular weight cut off 3.5 kDa) was used to concentrate the CAO solution from the dialysis tubing. Following concentration to required volume, the filterate was lyophilized and stored at −40° C. until further use. Alternatively, CAO was recovered from the reaction mixture by precipitation (twice) with ethanol.

2.2. Determination of the Oxidation State of CA and Derivatives

Qualitative estimation of the degree of colominic acid oxidation was carried out with 2,4 dinitrophenylhydrazine (2,4-DNPH), which yields sparingly soluble 2,4 dinitrophenyl-hydrazones on interaction with carbonyl compounds. Non-oxidised (CA)/oxidised (CAO) were added to the 2,4-DNPH reagent (1.0 ml), the solutions were shaken and then allowed to stand at 37° C. until a crystalline precipitate was observed [Shriner et. al., 1980]. The degree (quantitative) of CA oxidation was measured with a method [Park and Johnson, 1949] based on the reduction of ferricyanide ions in alkaline solution to ferric ferrocyanide (Persian blue), which is then measured at 630 nm. In this instance, glucose was used as a standard.

2.3. Gel Permeation Chromatography

Colominic acid samples (CA and CAO) were dissolved in $NaNO_3$ (0.2M), $CH_3CN$ (10%; 5 mg/ml) and were chromatographed on over 2×$GMPW_{XL}$ columns with detection by refractive index (GPC system: VE1121 GPC solvent pump, VE3580 RI detector and collation with Trisec 3 software Viscotek Europe Ltd). Samples (5 mg/ml) were filtered over 0.45 μm nylon membrane and run at 0.7 cm/min with 0.2 M NaNO3 and $CH_3CN$ (10%) as the mobile phase.

Figure 1:
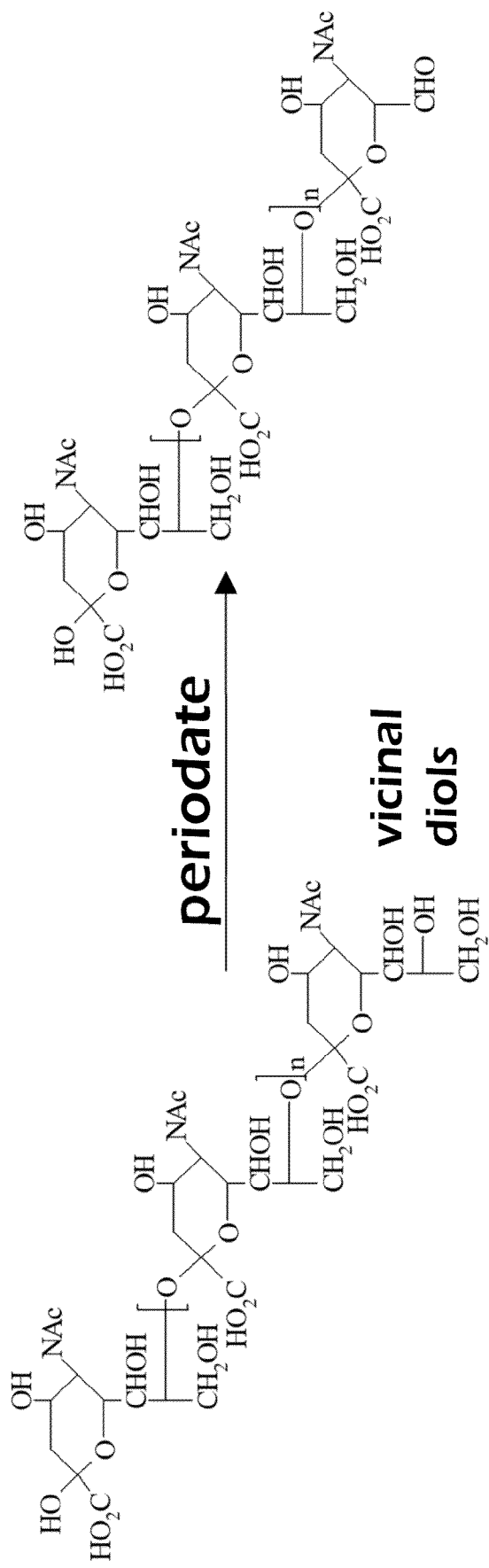
FIG. 1 is a reaction scheme showing the prior art activation of the non-reducing sialic acid terminal unit.
Figure 2:
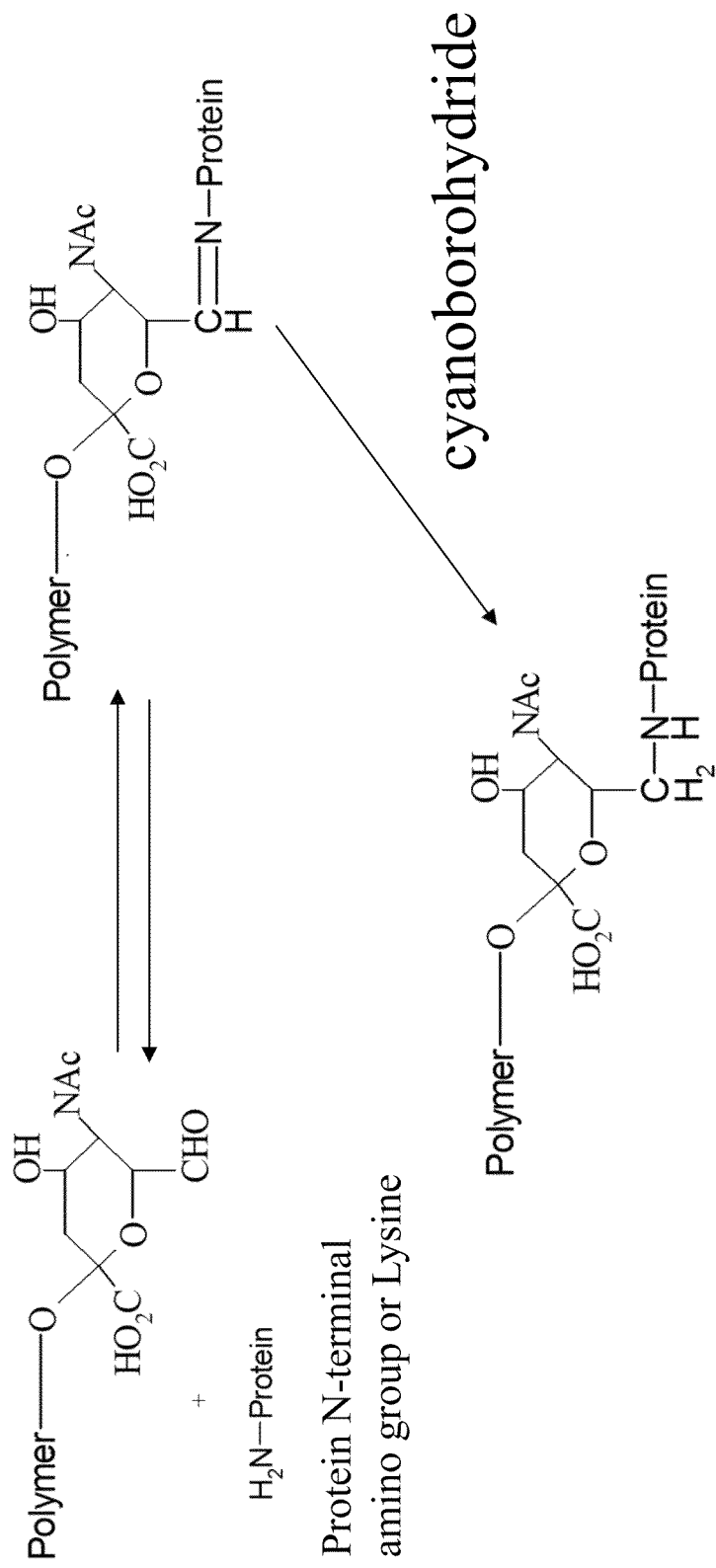
FIG. 2 is a reaction scheme showing the N-terminal or random derivatisation of proteins.
Figure 3A:
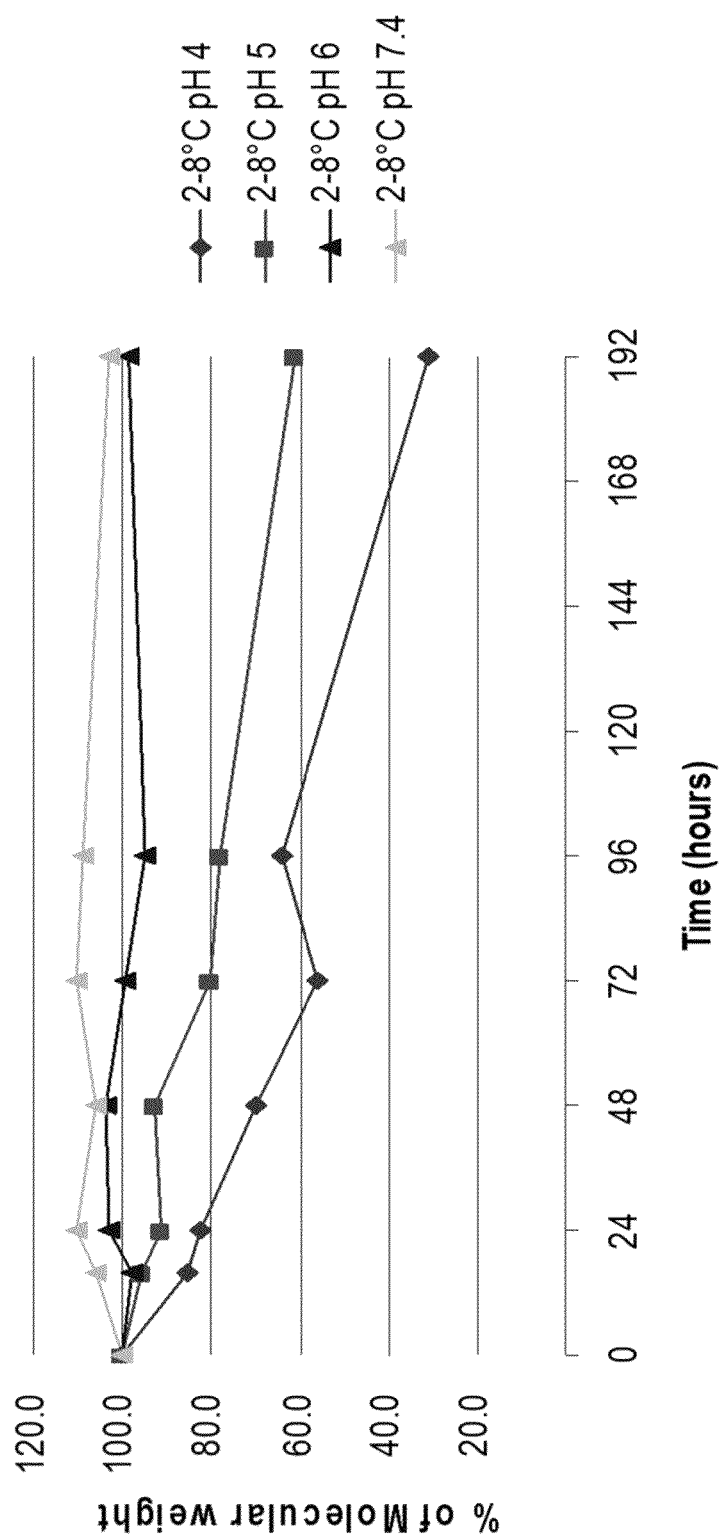
FIG. 3a shows the degradation of 24 kDa colominic acid (CA) at different pHs using Triple Detection GPC (Viscotek: RI+RALS+Viscosiometer)
Figure 3B:
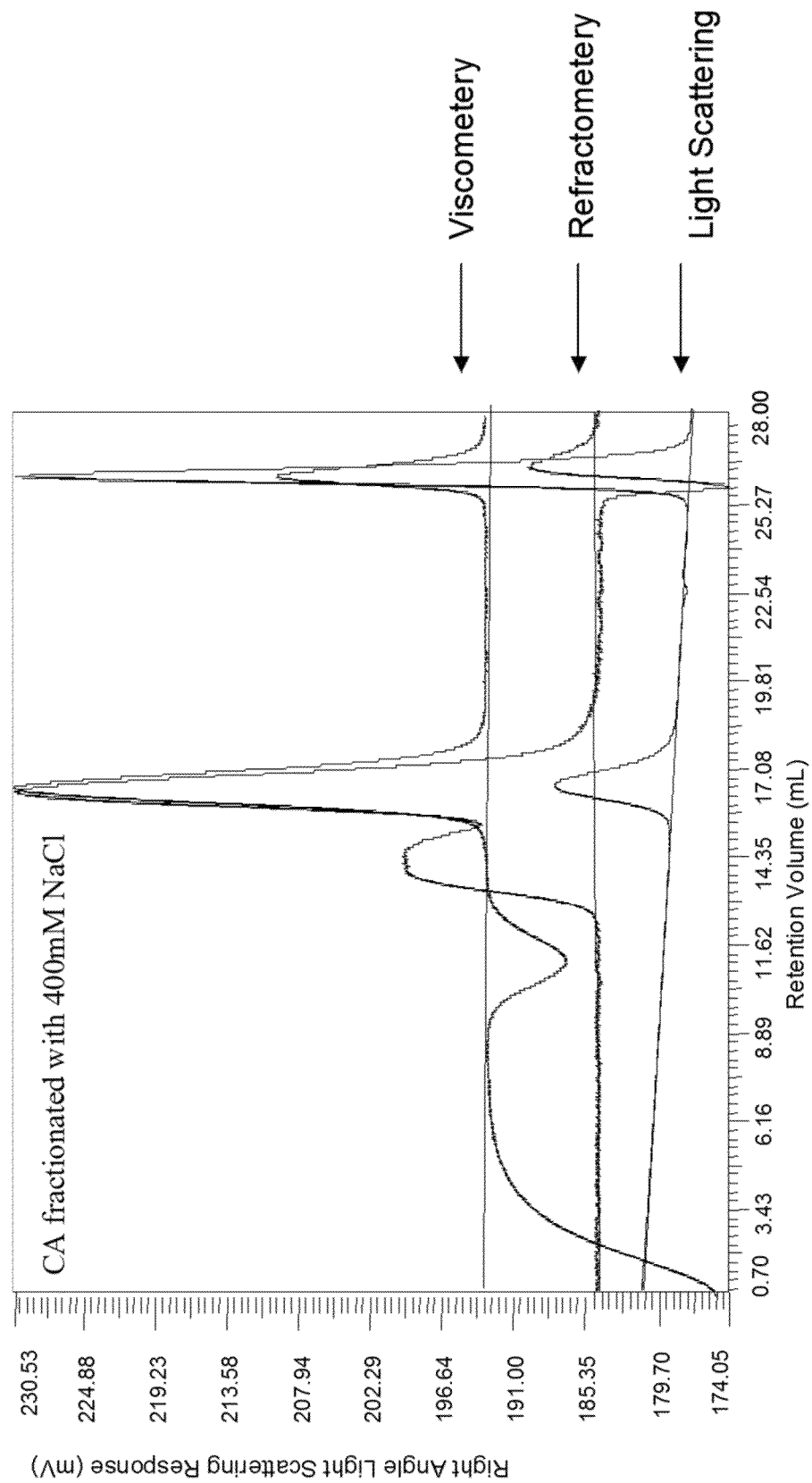
FIG. 3b shows Gel Permeation chromatography of the CA polymer.

The results are shown in FIG. 3b and tables 5 and 6.

2.4. Colominic Acid Stability

The rules for chemistry of the PEGylation cannot be applied to polysialylation as such because of the difference in the physiochemical properties of these molecules. PSA is an acid labile polymer and is stable for weeks around neutral pH (FIG. 3a). The results in FIG. 3a show that at pH 6.0 and 7.4 CA is stable for 8 days, at pH 5.0 there is slow degradation (after 48 hours 92% of initial MW), and at pH 4.0 there is slow degradation (after 48 hours 70% of initial MW). Polysialic acid is highly hydrophilic whereas PEG is amphiphilic. When the polysialylation is carried out using conditions used for PEGylation, aggregation and precipitation of the proteins is seen in many cases.

3. Preparation of N-Terminal Protein-CA Conjugates with Formulation Additives

3.1. Preparation of EPO-CA Conjugates (N-Terminal Method)

EPO was supplied as a solution (0.34 mg/ml in 10 mM sodium phosphate buffer 130 mM NaCl pH 7.0; specific activity: 110,000 U/mg, m.w. 30600) and stored at −32° C., protein was defrosted at 2-8° C. and required amount was taken into a 2 ml eppendorf tube. The required amount (25 fold molar excess) of colominic acid was taken and the protein solution was added to solid CA and mixed gently. The required volume of sodium cyanoborohydride solution was added to have 50 mM or 3.17 mg/ml in the reaction mixture, vortex and check the pH of the final reaction mixture; if necessary adjust the pH to 6.0. Tube was sealed and stirred at desired temperature for 24 hours or the reaction mixture was first incubated at RT (22° C.) for 8 hours and then kept at 4±1° C. overnight (14 hours). After incubation, the necessary samples were taken (e.g. for activity assay, SDS-PAGE, SE-HPLC).

3.1.1 Purification and Characterization of EPO-CA Conjugates (N-Terminal Method)

The remaining reaction mixture sample was diluted with HIC buffer A1 (3 M Ammonium sulphate, pH 6.3) so that a final concentration of 2 M results and loaded on the HIC column previously equilibrated with HIC buffer A at the rate of 1.5 ml/min at RT. Loading fraction collected and labeled. Column was washed with HIC buffer A2 (2M Ammonium sulphate, pH 6.3) (at least 6 column volume) fractions collected and labeled. The product was eluted with HIC buffer B (50 mM $Na_2HPO_4$ pH 7.4), first fraction (0.5 ml) and then 0.5-1 ml fractions (6CV) were collected and labeled. Samples were kept on ice (4±1° C.) during purification.

The protein concentration was analysed by UV (280 nm) (Abs of 1 mg/ml of EPO is about 0.743). The samples were taken for SDS-PAGE. The separation of non-conjugated EPO was performed using anion exchange chromatography (AEC) if CA Mw is too small (e.g. 22KDa) for separation of conjugate and EPO by SE-HPLC. For AEC the HIC fractions containing protein were diluted with AEC buffer A (50 mM Tris, 150 mM NaCl pH 8.0) (1 ml sample+5 ml AEC buffer A) and loaded to the EC column pre-equilibrated with AEC buffer A at 1.0 ml/min. Loading fractions were collected and labeled. Column was washed with AEC buffer A (at least 10 ml) fractions collected and labeled. Eluted the product with elution buffer B (50 mM Tris, 600 mM NaCl, pH 8.0), first fraction of 0.5 ml and then 0.5-1 ml fractions at 2.0 ml/min were collected and labeled. Samples were kept on ice during purification.

Alternatively purification can be done by SE-HPLC (e.g. to separate conjugates from EPO if CA used has high molecular weight, e.g. 39kDa). The protein concentration was analysed by UV (280 nm) (Abs of 1 mg/ml of EPO is about 0.743). Samples were taken for SDS-PAGE.

An aliquot was removed for protein assay and CA assay. The remaining solution was stored at −20° C. until use. Products were characterised by SDS-PAGE. To determine the activity of EPO and NG EPO samples in inducing proliferation in vitro of erythrocyte progenitor cells isolated from the spleen of a mouse rendered anaemic artificially through I.P. injection of phenylhydrazine was used. The protocol was adapted based on the method reported by Krystal [1972]. The assay depends on adding EPO to erythrocyte progenitors and measuring the rate of DNA replication by determining the rate of incorporation of $^3H$-thymidine. The in vivo pharmacokinetics (PK) and pharmacodynamics (PD) studies were done in B6D2F1 mice.

3.2. Preparation of EPO-CA Conjugates (Random)

EPO was supplied as a solution (0.34 mg/ml in 10 mM sodium phosphate buffer 130 mM NaCl pH 7.0; specific activity: 110,000 U/mg, m.w. 30600) and stored at −32° C., protein was defrosted at 2-8° C. and required amount was taken into a 2 ml Eppendorf tube. The required amount of colominic acid was taken and the protein solution was added to solid CA and mixed gently. The required volume of sodium cyanoborohydride solution was added to have 50 mM or 3.17 mg/ml in the reaction mixture, vortex and check the pH of the final reaction mixture; if necessary adjust the pH to 7.4. The tube was sealed and stirred at desired temperature (4±1° C.) for 24 hours. After incubation, the necessary samples were taken (e.g. for activity assay, SDS-PAGE, SE-HPLC).

3.2.1. Purification and Characterization of EPO-CA Conjugates (Random)

The remaining reaction mixture sample was diluted with HIC buffer A1 (3 M Ammonium sulphate, pH 6.3) so that a final concentration of 2 M results and loaded on the HIC column previously equilibrated with HIC buffer A at the rate of 1.5 ml/min at RT. Loading fraction was collected and labeled. The column was washed with HIC buffer A2 (2 M Ammonium sulphate, pH 6.3) (at least 6 column volume), washing fractions were collected and labeled. Eluted the product with HIC buffer B (50 mM $Na_2HPO_4$ pH 7.4), first fraction of 0.5 ml and then 0.5-1 ml fractions (6CV) were collected and labeled. Samples were kept on ice (4±1° C.) during purification.

The protein concentration was analysed by UV (280 nm) (Abs of 1 mg/ml of EPO is about 0.743). The samples were taken for SDS-PAGE. The separation of non-conjugated EPO was performed using anion exchange chromatography (AXC) if CA Mw is too small (e.g. 22KDa) for separation of conjugate and EPO by SE-HPLC. For AXC the HIC fractions containing protein were diluted with AXC buffer A (50 mM Tris, 150 mM NaCl pH 8.0) (1 ml sample+5 ml AXC buffer A) and loaded to the AXC column pre-equilibrated with AXC buffer A at 1.0 ml/min. The loading fractions were collected and labeled. Column was washed with AXC buffer A (at least 10 ml) fractions were collected and labeled. The product was eluted with elution buffer (50 mM Tris, 600 mM NaCl, pH 8.0), first fraction collected (0.5 ml) and then 0.5-1 ml fractions at 2.0 ml/min and labeled. Samples were kept on ice during purification.

Alternative purification can be done by SE-HPLC (e.g. to separate conjugates from EPO if CA used has high molecular weight, e.g. 39kDa). The protein concentration was analysed by UV (280 nm) (Abs of 1 mg/ml of EPO is about 0.743). The samples were taken for SDS-PAGE.

3.3. Glycon Chemistry

Hydrazide colominic acid was dissolved in the EPO solution to get the final CA concentration of 10 mM. The pH of the solution was adjusted to 5.5. The required volume of NaIO4 solution in NaOAc solution was added to get the final concentration of 5 mM NaIO4. The reaction was stopped with NaHSO3 (final concentration of NaHSO3 to be 20 mM). The reaction mixture was incubated at room temperature. Finally the required volume of NaCNBH3 solution in NaOAc solution was added to give the final concentration of 50 mM NaCNBH3. The reaction was continued at 4±1° C. on shaker for one hour. After incubation the necessary samples were taken for SDS, SE-HPLC, activity assay.

3.3.1. Purification and Characterization of EPO-CA Conjugates (Glycon Chemistry)

The remaining reaction mixture sample was diluted with HIC buffer A1 (3 M Ammonium sulphate, pH 6.3) so that a final concentration of 2 M results and loaded on the HIC column previously equilibrated with HIC buffer A at the rate of 1.5 ml/min at RT. Loading fraction collected and labeled ($L_1$-$L_x$). The column was washed with HIC buffer A2 (2 M Ammonium sulphate, pH 6.3) (at least 6 column volume) and the fractions were collected and labeled. The product was eluted with HIC buffer B (50 mM $Na_2HPO_4$ pH 7.4), first fraction of 0.5 ml and then 0.5-1 ml fractions (6CV) were collected and labeled. Samples were kept on ice (4±1° C.) during purification.

The protein concentration was analysed by UV (276 nm) (Abs of 1 mg/ml of EPO was about 0.743). The samples were taken for SDS-PAGE. The separation of non-conjugated EPO was performed using anion exchange chromatography (AXC) if CA Mw is too small (e.g. 22KDa) for separation of conjugate and EPO by SE-HPLC. For AXC the HIC fractions containing protein were diluted with AXC buffer A (50 mM Tris, 150 mM NaCl pH 8.0) (1 ml sample+5 ml AXC buffer A) and loaded to the AXC column pre-equilibrated with AXC buffer A at 1.0 ml/min. The loading fractions were collected and labeled. The column was washed with AXC buffer A (at least 10 ml) and the fractions were collected and labeled. The product was eluted with elution buffer (50 mM Tris, 600 mM NaCl, pH 8.0), first fraction of 0.5 ml and then 0.5-1 ml fractions at 2.0 ml/min were collected and labeled. Samples were kept on ice during purification.

Alternative purification can be done by SE-HPLC (e.g. to separate conjugates from EPO if CA used has high molecular weight, e.g. 39kDa). The protein concentration was analysed by UV (280 nm) (Abs of 1 mg/ml of EPO is about 0.743). The samples were taken for SDS-PAGE.

3.4. PEGylation of EPO:

EPO (30.6kDa) was supplied as a solution (0.954 mg/ml in 10 mM sodium acetate buffer, pH 4.0 containing 5% sorbitol, 0.025 mg/ml polysorbate 80) and stored at 2-8° C. EPO solution was concentrated to make about 1.0 mg/ml of solution. The required amount of EPO was taken into an Eppendorf tube and placed on ice. The amount of PEG added for conjugation was calculated based on formula:

$$\text{Weight of } PEG = \frac{\text{Amount of protein (g)}}{(\text{MW of protein})} \times (\text{MW of } PEG) \times (\text{Molar excess of } PEG)$$

Figure 5A:
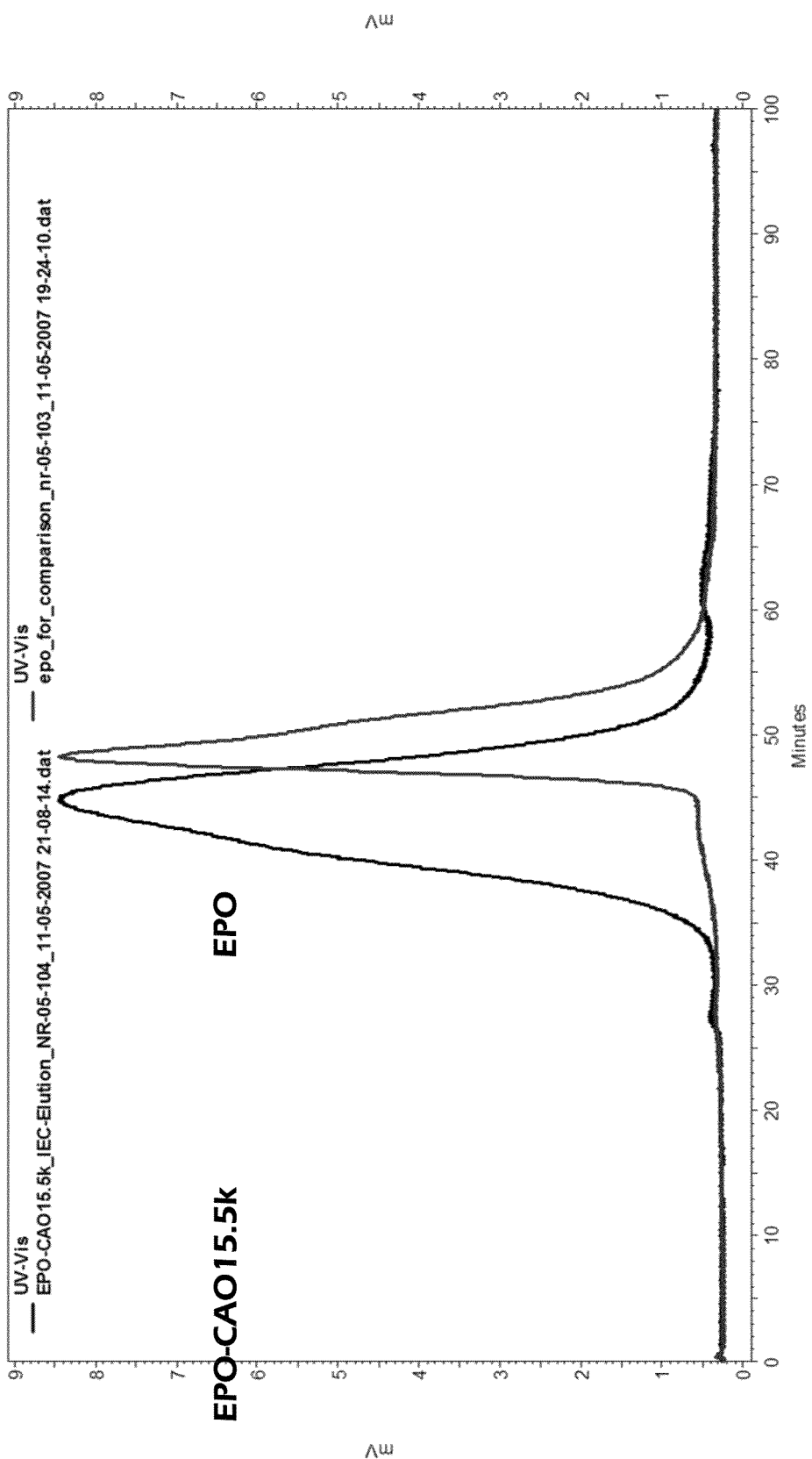
FIGS. 5a and 5b show the characterisation of polysialylated EPO by SDS-PAGE and SE-HPLC.
Figure 5B:
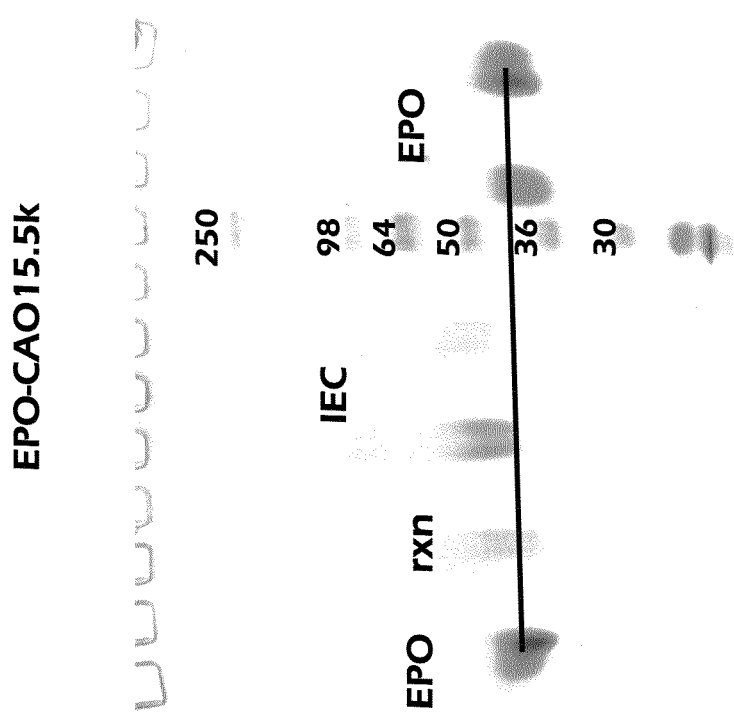
Figure 6A:
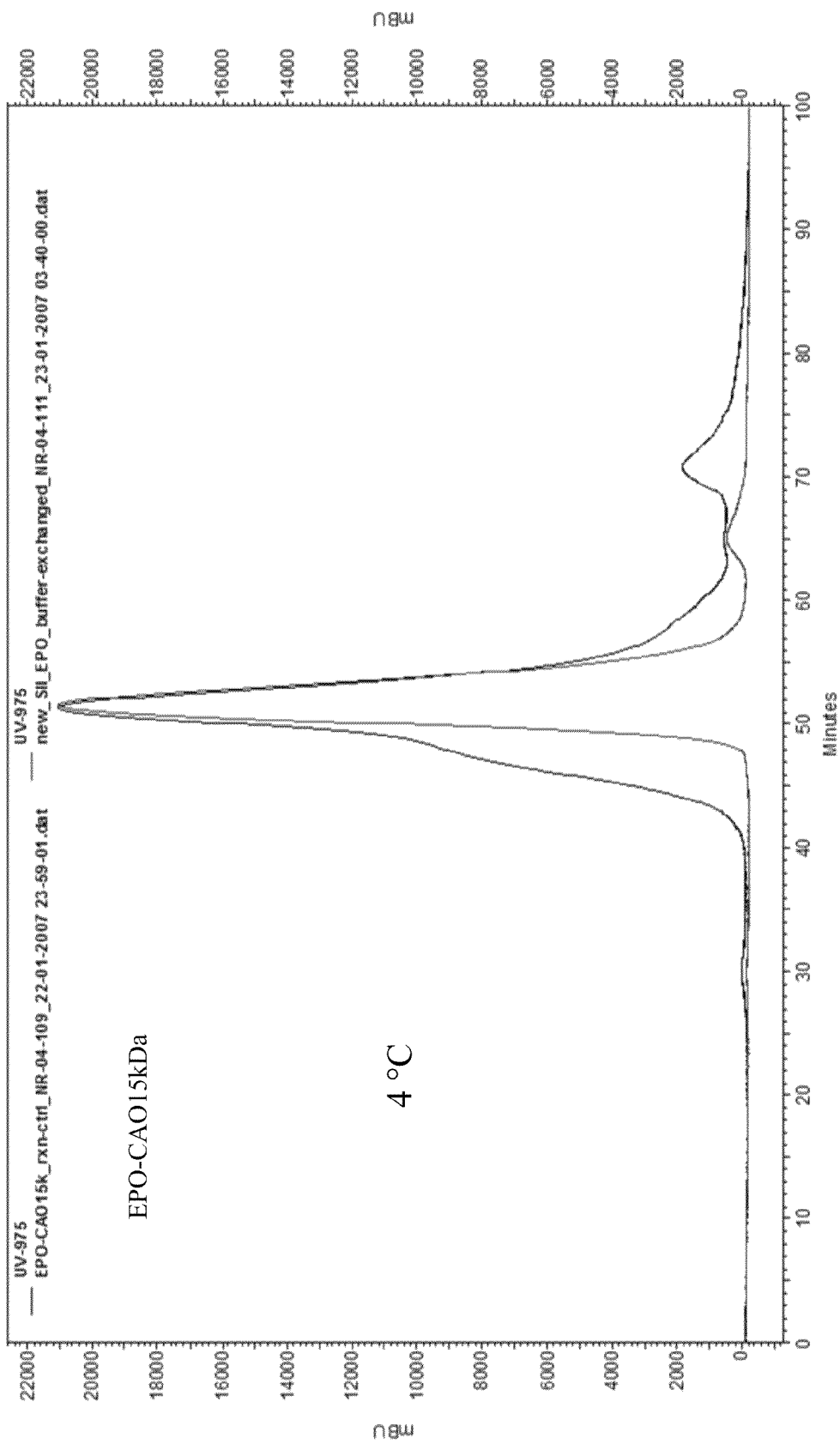
Figure 6B:
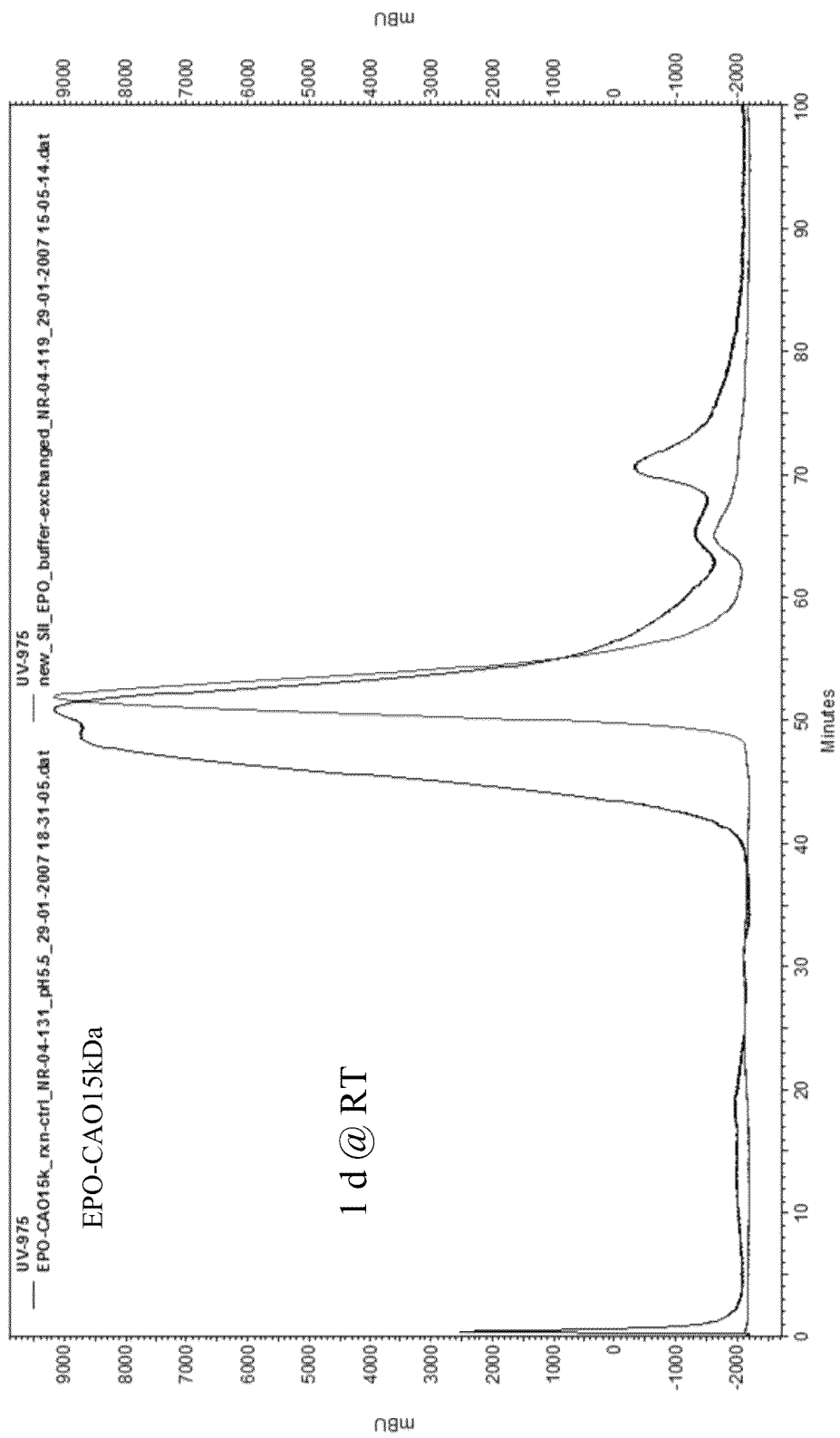
Figure 6C:
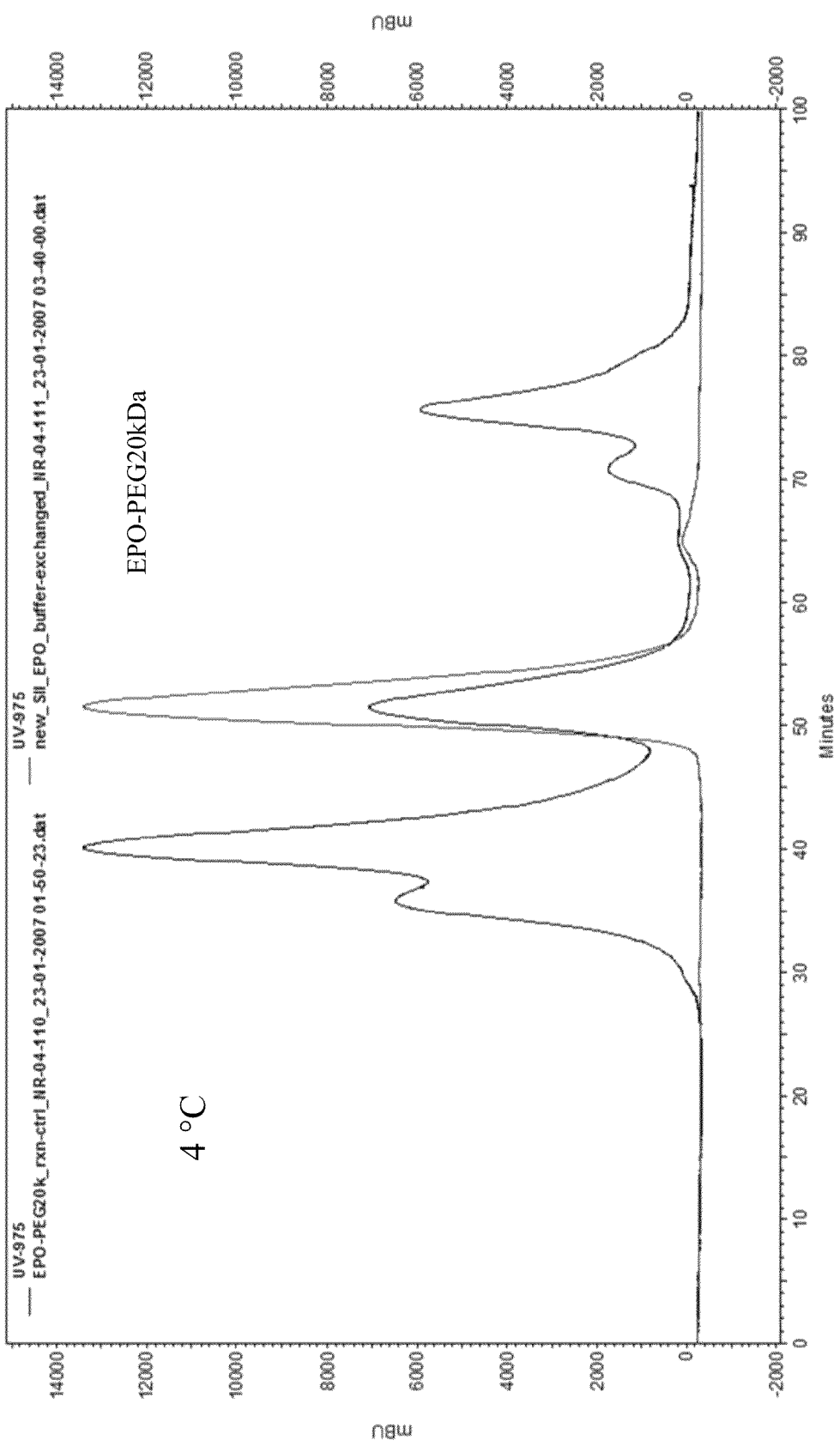
Figure 6D:
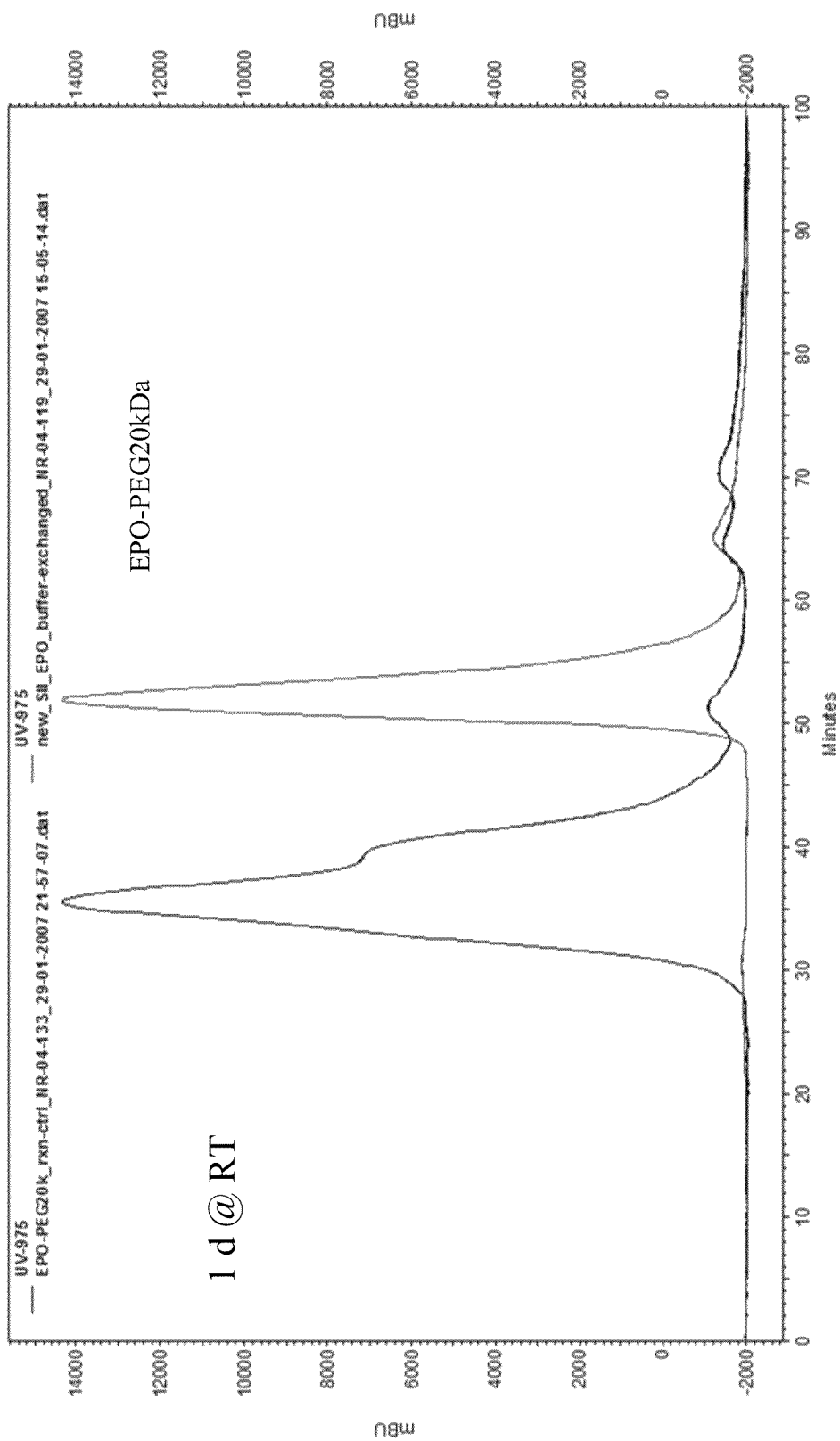

The required amount of PEG 20K was weighed out. It was solubilised in 10 mM NaOAc, 5% sorbitol, pH 5.5 (20% volume of the final reaction volume as used here), the mixture was gently vortexed until all the PEG had dissolved and then either filtered into a new eppendorf or centrifuged at 4000 rpm for 5 min and the supernatant was transferred to a new eppendorf to remove any aggregated/precipitated material. Required amount of EPO protein solution was added to the PEG solution to give a 25 fold molar excess of PEG and was gently mixed by keeping the reaction mixture on a gentle shaker at 4±1° C. Required volume of 100 mg/ml NaCNBH3 solution was added in order to have 50 mM or 3.17 mg/ml in the final reaction mixture, gently mixed and the pH of the final reaction mixture was checked, and if necessary adjusted to 5.5 with 1 M NaOH/HCL at 4±1° C. Finally the volume of the reaction was adjusted using 20 mM NaOAC, 5% sorbitol, and pH 5.5 to give a protein concentration of 1 mg/ml in the reaction mixture. The tube was sealed and stirred at desired temperature (4±1° C.) for 24 hours. The reaction was stopped by an appropriate method and samples were taken out for in vitro activity, SDS-PAGE (using 4-20% Tris-glycine gel), SE-HPLC (superose 6 column) and checked the pH of reaction mixture. To eliminate any precipitate the reaction mixture was centrifuged at 13000 rpm for 5 min before SE-HPLC analysis and purification, preferred buffer for SE-HPLC was 0.1 M sodium phosphate (pH 6.9). The results are shown in FIG. 5.

3.5 Preparation of N-Terminal Non-Glycosylated Erythropoietin (NG EPO-CA) Conjugates NG EPO was supplied as a solution (0.18 mg/ml in 20 mM sodium phosphate buffer 300 mM NaCl pH 6.65; specific activity 100000 U/mg; m.w. 19000) and stored at −32° C., protein defrosted at 2-8° C. and taken the required amount into a 2 ml eppendorf. The amount of colominic acid (e.g. oxidised or non-oxidised colominic acid) required for conjugation was calculated. The required amount of colominic acid was weighed out Protein solution was added to solid CA and mixed gently. The required volume of sodium cyanoborohydride solution was added to the reaction mixture so that the final concentration of sodium cyanoborohydride should be 50 mM or 3.17 mg/ml in the reaction mixture. The final reaction mixture was vortexed and checked the pH; if necessary the pH was adjusted to 7.4. The tube was sealed and stirred at desired temperature (4±1° C.) for 24 hours. After incubation, the necessary samples were taken for activity assay, SDS-PAGE, SE-HPLC etc.

3.5.1 Purification and Characterization of NG EPO-CA Conjugates

The remaining reaction mixture sample was diluted with HIC buffer A (1.2 M Ammonium sulphate, pH 6.3) (1 ml sample+4 ml of buffer A) and loaded on the HIC column previously equilibrated with HIC buffer A. The loading fractions were collected and labeled. The column was washed with HIC buffer A (at least 10 ml). The washing fractions were collected and labeled. The product was eluted with HIC buffer B, first fraction of 0.5 ml and then 0.5-1 ml fractions were collected and labeled. Samples were kept on ice during purification. The protein concentration was analysed by UV (280 nm) (Abs of 1 mg/ml of nEPO was about 0.743). The samples were taken for SDS-PAGE. The reaction conditions led to no significant free NG EPO in the reaction mixture so no further purification was necessary. If NG EPO was present in the reaction mixture, the HIC fractions containing protein were concentrated using Vivaspin 6 (5000 MWCO) and purification was done by SE-HPLC. The protein concentration was analysed by UV (280 nm) (Abs of 1 mg/ml of NG EPO is about 0.743). The samples were taken for SDS-PAGE.

An aliquot was removed for protein assay and CA assay. Stored the remainder at −20° C. until use. Product was characterised by SDS-PAGE.

3.6. SE-HPLC of EPO Formulations

HPLC was performed on a Liquid Chromatograph (Jasco) equipped with a Jasco, AS-2057 plus autosampler refrigerated at 4° C., and a Jasco UV-975 UV/VIS detector. Data was recorded by EZchrom Elite software on an IBM/PC. The SEC samples were analysed with an isocratic mobile phase of 0.1 M Na phosphate, pH 6.9; on a Superose 6 column (FIG. 5). FIG. 6 shows just one peak at RT=76.408, which is attributed to EPO.

The peak table for the SEC shown on the left hand side of FIG. 5 is as follows:

TABLE 1

| Peak | RT | % Area | Species |
|---|---|---|---|
| 1 | 33.896 | 13.9 | Aggregate |
| 2 | 60.871 | 85.7 | CA38K-EPO |
| 3 | 76.229 | 0.4 | EPO |

3.7. SDS Polyacrylamide Gel Electrophoresis, Western Blotting & ELISA

Figure 4:
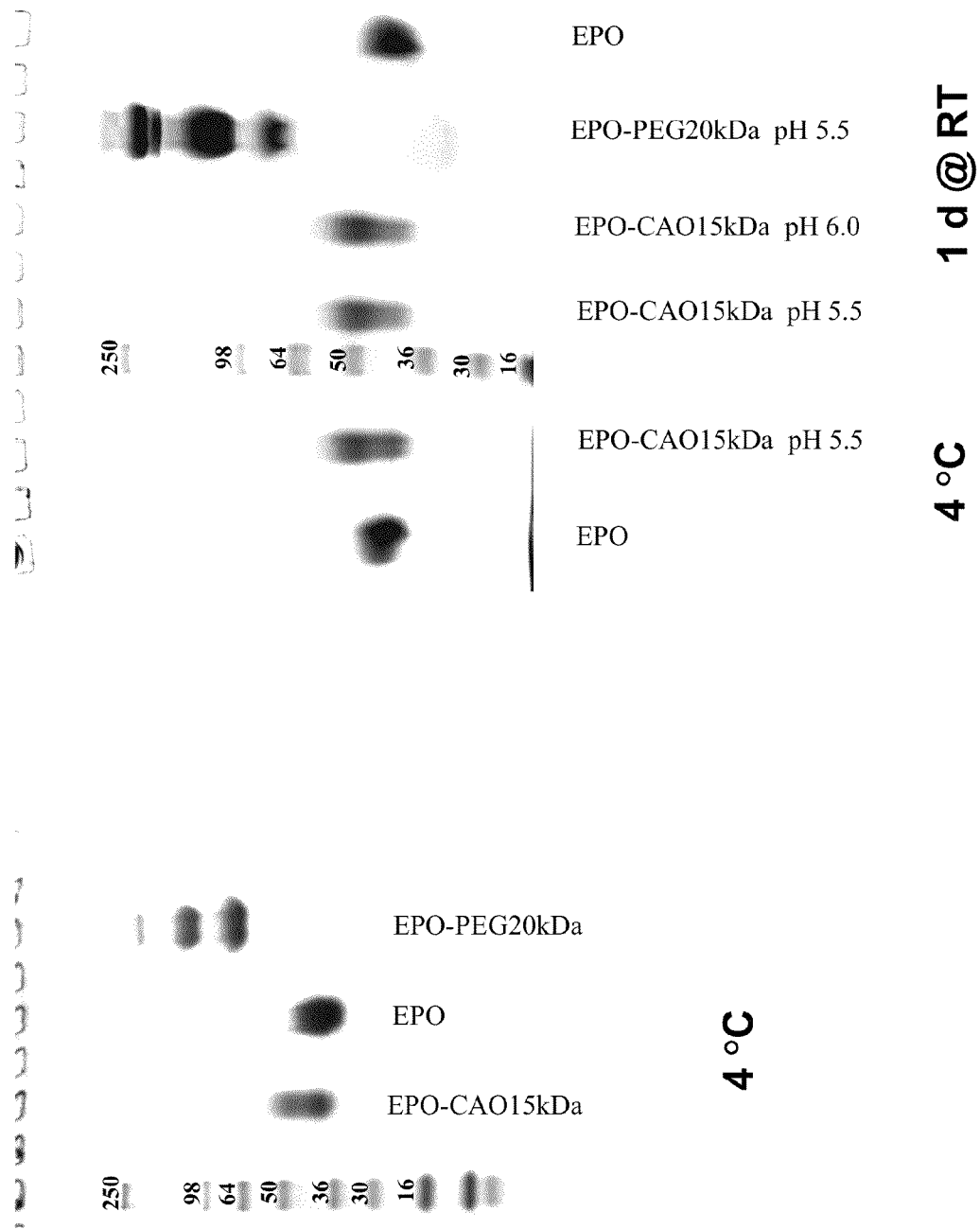
FIG. 4 shows the characterisation of PEGylated and polysialylated EPO by SDS-PAGE.

SDS-PAGE was performed using 4-20% trisglycine gels. Samples were diluted with either reducing or non reducing buffer and 5.0 ug of protein was loaded into each well. The gels were run on a triglycerine buffer system and was stained with Coomassie Blue. Western blotting was performed using anti PSA antibody (FIG. 4). FIG. 4 shows the SDS-PAGE of EPO formulations (site-specific; N-terminal).

3.8. In Vitro Activity

To determine the activity of EPO samples in inducing proliferation in vitro of erythrocyte progenitor cells isolated from the spleen of a mouse rendered anaemic artificially through I.P. injection of phenylhydrazine was used. The protocol was adapted based on the method reported by Krystal [1972]. The assay depends on adding EPO to erythrocyte progenitors and measuring the rate of DNA replication by determining the rate of incorporation of $^3$H-thymidine.

3.9. Stability Studies

Sterile EPO conjugates were stored in 20 mM sodium phosphate, pH 7.4; 5% sorbitol and 0.025 mg/ml Tween 20; at 4° C. for six weeks. SE-HPLC of the samples was performed using SEC columns under following conditions: Injection volume 100 ul, flow rate 0.250 ml/min, running buffer 0.1 M sodium phosphate, pH 6.9.

3.10. In Vivo Efficacy of EPO Formulations

The in vivo efficacy of EPO formulations was studied in female mice B6D2F1, 7-8 weeks old, 5-15 ugs of protein dose (same activity) was injected in mice subcutaneously. Animals were divided into seven groups of four. EPO formulations were given to each animal of each group in the following manner; EPO, EPO-PSA conjugates, PBS, Aranesp (5 µg). 50 µl of blood was taken from each animal and was analysed by FACS after staining with retic count dye (FIGS. 8 and 9).

5 µl of well mixed whole blood was mixed with 1 ml of Retic-Count reagent and incubated at room temperature for 30 minutes in the dark. Samples were then analysed with the help of FACS machine by counting the reticulocytes.

3.11. Elisa

EPO-PSA was captured by the anti-PSA antibody coated over the plate. Captured EPO-PSA was detected with anti-EPO antibody so that only EPO conjugated with PSA was detected.

3.12. In Vivo Clearance

In vivo clearance of EPO formulation was studied on mice. Appropriate amount of protein dose was injected to the mice subcutaneously and intravenously. EPO formulations were radiolabelled with $^{125}$I and the radioactivity of the blood sample was measured at frequent intervals.

Results

Activation of CA and Determination of Degree of Oxidation

Colominic acid (CA), a linear alpha-2,8-linked homopolymer of N-acetylneuraminic acid (Neu5Ac) residues was used. Exposure of colominic acids to oxidation was carried out for 15 min using 20 mM periodate at room temperature. The integrity of the internal alpha-2,8 linked Neu5Ac residues post periodate treatment was analysed by gel permeation chromatography and the chromatographs obtained for the oxidised (CAO), material was compared with that of native CA. It was found that oxidized and native CA exhibit almost identical elution profiles, with no evidence that the successive oxidation step give rise to significant fragmentation of the polymer chain.

Quantitative measurement of the oxidation state of CA was performed by ferricyanide ion reduction in alkaline solution to ferrocyanide (Prussian Blue) [Park and Johnson, 1949] using glucose as a standard. Table 1 shows that the oxidized colominic acid was found to have a greater than stoichiometric (>100%) amount of reducing agent, i.e. 112 mol % of apparent aldehyde content comprising the combined reducing power of the reducing end hemiketal and the introduced aldehyde (at the other end, non reducing end).

TABLE 2

Degree of oxidation of various colominic acid intermediates in the double oxidation reaction scheme using glucose as a standard (100%, 1 mole of aldehyde per mole of glucose; n = 3 ± s.d).

| CA species | Degree of oxidation |
|---|---|
| colominic acid (CA) | 16.1 ± 0.63 |
| colominic acid-oxidised (CAO) | 112.03 ± 4.97 |
| colominic acid-reduced (CAOR) | 0; Not detectable |
| colominic acid-oxidised-reduced-oxidised (CAORO) | 95.47 ± 7.11 |

Preparation, Purification and Characterisation of EPO Conjugates

The procedure to prepare and purify colominic acid (CA) conjugates of Erythropoietin (EPO) in an N-terminally selective manner by conducting the reaction at a reduced pH (pH 5.5) and random pH (7.4) and at 4±1° C. is detailed above. This involves conjugation in the presence of sodium cyanoborohydride, followed by purification using ion-exchange chromatography (AEX) to remove free EPO followed by removal of CA by hydrophobic interaction chromatography (HIC). The low pH was used to favour selective derivatisation of the alpha amino group of the N-terminus, and also in order to minimise aggregation of EPO during the reaction. The composition of the final reaction buffer was 5% sorbitol, 0.5 mg/ml Tween 20 in 10 mM NaOAc at pH 5.5.

Formation of the EPO-CA conjugates was confirmed by the SE-HPLC (change of retention time of EPO-CA as compared to EPO; also co-elution of both moieties); ion exchange chromatography (binding of conjugates on to the AEC column) and polyacrylamide gel electrophoresis (SDS-PAGE; broadening and shifting of bands upwards with high m.w. species) (FIG. 4). The polysialyted samples were active in vitro and showed vastly superior profile (PK and PD) to plain EPO. FIGS. 11 and 12 show in vivo results.

FIG. 5, left hand side, shows the SE-HPLC of EPO-CA 39kDa conjugation after 24 hours. Table 3 is the peak analysis table. Characterisation conditions: column Superdex 200, buffer ammonium bicarbonate 0.15 M, pH 7.8.

TABLE 3

| Peak | RT | % Ar | Species |
|---|---|---|---|
| 1 | 31.421 | 3.38 | Aggregate |
| 2 | 48.346 | 80.76 | CA39-EPO |
| 3 | 59.204 | 15.86 | EPO |

Degree of derivatisation was found to be more in the PEGylated EPO than the polysialylated EPO (FIG. 6). This may be due to the inert nature of PEG and charged nature of sialic acid. Reticulocyte count from FACS data was more for PSA-EPO conjugate than the EPO (FIG. 7). After purification of the EPO-CAO conjugate no significant EPO was seen on the chromatogram from SEC HPLC and the derivatisation was proved by the change of retention time on SE-HPLC and broadening and shifting of bands with higher molecular weight on SDS PAGE. Polysialylation of EPO was also shown by western blotting using murine anti PSA antibody. In vivo clearance profile of PSA-EPO conjugate was found to be superior as compared to EPO (FIG. 8) when given IV and the area under the curve was increased by 7.1 fold. Similarly subcutaneous dose of EPO-PSA also shows greater retention as compared to EPO and the area under the curve was increased by 2.5 fold. Polysialylation of EPO was also found to be proportional to incubation time for reaction mixture, molar excess and pH. In vivo clearance profile (intravenous and subcutaneous) for polysialylated NG EPO was found to be better than the NG EPO (FIGS. 11 and 12). In some SDS gels dipolysialylation of EPO was also seen. EPO-PSA conjugates were also confirmed by the ELISA method (FIGS. 14 and 15). Erythropoiesis phenomenon was found to be greater with the EPO-PSA conjugate as compared to the EPO and was found to be proportional to the molecular weight of the polymer from 6 to 15KDa (FIG. 18). 15KDa was found to be the optimal chain length for EPO as with heavier chains of sialic acid phenomenon of erythropoiesis reduces. This may be due to the negatively charged nature of the polymer resulting in the repulsion from the receptor. This study was confirmed with the help of FIG. 18. Emax of Aranesp was found to be much greater than EPO-PSA which is not clinically good and leads to thrombosis and could cause exhaustion of bone marrow and was also found to lower the reticulocytes below the baseline after the treatment. EPO-PSA was found to be vastly superior than the EPO and EPO-PSA was found to be as good as EPO-PEG and EPO-PSA also leads to constant erythropoiesis.

The PSA conjugates were found to be active in the in vitro activity assay. In vivo efficacy study shows that PSA-EPO conjugates are as good as PEG conjugates and vastly superior to EPO (FIGS. 8 and 9)

Formation of the NG EPO-CA conjugates was confirmed by the SE-HPLC (change of retention time of NG EPO-CA as compared to NGEPO; also co-elution of both moieties); ion exchange chromatography (binding of conjugates on to the AEC column) and polyacrylamide gel electrophoresis (SDS-PAGE; shifting of bands with high m.w. species). The Figures show that EPO-CA 39kDa conjugation after 24 hours. The polysialyted samples were active in vitro and showed vastly superior profile (PK and PD) to plain NGepo.

FIG. 10 shows the SE-HPLC results. The peak analysis is shown in table 4 below. Characterisation conditions—column Superdex 200, buffer ammonium bicarbonate 0.15 M, pH 7.8.

TABLE 4

| Peak | RT | % Ar | Species |
|---|---|---|---|
| 1 | 31.863 | 3.41 | aggregate |
| 2 | 33.212 | 6.65 | aggregate |
| 3 | 42.667 | 14.72 | (CA)2-nEPO |
| 4 | 48.571 | 74.49 | CA-nEPO |
| 5 | 68.183 | 0.73 | nEPO |

FIG. 12 shows the in vivo clearance results. PSA-NG EPO showed a vastly superior profile as compared to NG EPO.

Table 5 shows values of various parameters used and table 6 gives the molecular weight and polydispersity of CA fractions.

TABLE 5

| Parameters | Values |
|---|---|
| Mn (Da) | 26,666 |
| Mw (Da) | 27,956 |
| Mz (Da) | 31,129 |
| Mp (Da) | 22,969 |
| Mw/Mn | 1.048 |
| IV (dl/g) | 0.2395 |
| Rh (nm) | 4.683 |
| Branches | 0.00 |
| Sample Conc (mg/ml) | 5.600 |
| Sample Recovery (%) | 90.71 |
| dn/dc (ml/g) | 0.156 |
| dA/dc (ml/g) | 0.000 |
| Mark-Houwink a | −0.048 |
| Mark-Houwink logK | −0.425 |

TABLE 6

| CA fraction | Mw (kDa) | pd |
|---|---|---|
| 475 | 97.2 | 1.285 |
| 450 | 52.3 | 1.109 |
| 425 | 37.9 | 1.062 |
| 400 | 28.0 | 1.048 |

TABLE 6-continued

| CA fraction | Mw (kDa) | pd |
|---|---|---|
| 375 | 19.0 | 1.080 |
| *350 | 14.5 | — |
| *300 | 10.0 | — |
| *250 | 7.0 | — |

References

Fernandes, A. I., Gregoriadis, G., Synthesis, characterization and properties of polysialylated catalase, Biochimica et Biophysica Acta, 1293 (1996) 92-96

Fernandes, A. I., Gregoriadis, G., Polysialylated asparaginase: preparation, activity and pharmacokinetics, Biochimica et Biophysica Acta, 1341 (1997) 26-34.

Gregoriadis, G., McCormack, B., Wang, Z., Lifely, R., Polysialic acids: potential in drug delivery, FEBS Letters, 315 (1993) 271-276.

Jain et. al., Polysialylated insulin: synthesis, characterization and biological activity in vivo, Biochemica et. Biophysica Acta, 1622 (2003) 42-49.

Jain et. al., The natural way to improve the stability and pharmacokinetics of protein and peptide drugs. Drug delivery systems and sciences, 4(2), (2004) 3-9. Krystal Martindale, The extra pharmacopoeia, Thirty-first edition, Royal Pharmaceutical Society, London, 1996, 762-763.

Park, J. T., Johnson, M. J., A submicrodetermination of glucose, Journal of Biological Chemistry, 181 (1949) 149-151.

Shriner, R. L., Fuson, R. D. C., Curtin, D. Y., Morill, T. C., The Systematic Identification of Organic Compounds, 6th ed., Wiley, New York, 1980.

Svennerholm, L., Quantitative estimation of sialic acid II: A colorimetric resorcinol-hydrochloric acid method, Biochimca et Biophysica Acta, 24 (1957) 604-611.

Wang, W., Instability, stabilization, and formulation of liquid protein pharmaceuticals, International Journal of Pharmaceutics, 185(1999) 129-188.

Fan et al Exp Hematol. 2006 October; 34(10): 1303-11.

The invention claimed is:

1. A method of treating anemia in a patient comprising: administering a therapeutically effective amount of a composition comprising an amino-terminal polysialic acid (PSA) derivative of EPO and a pharmaceutically acceptable excipient to a patient in need thereof, wherein a PSA is attached to the amino-terminus of the EPO, and wherein the PSA comprises between 2 and 200 sialic acid units.

2. The method according to claim 1, wherein the composition is administered as an aqueous suspension in admixture with excipients.

3. The method according to claim 1, wherein the composition further comprises one or more dispersing or wetting agents, suspending agents, formulation additives, excipients, solubilizers, metal ions, buffers, stabilisers, surfactants, salts, polymers, metal ions, sugars, polyols or amino acids.

4. The method according to claim 3, wherein the stabilizer is selected from a sugar or a polyol, for example sucrose, sorbitol, trehalose, glycerol, mannitol, lactose, ethylene glycol, and sodium phosphate.

5. The method according to claim 3, wherein the solubiliser is a surfactant.

6. The method according to claim 3, wherein the metal ion is selected from $Zn^{2+}$, $Ni^{2+}$, $Co^{2+}$, $Sr^{2+}$, $Cu^{2+}$ and $Fe^{2+}$.

7. The method according to claim 3, wherein the formulation additive is a polymer selected from human serum albumin, PSA, PEG or hydroxy-beta-cyclodextrin.

8. The method according to claim 3, wherein the amino acids are selected from histidine, glycine, other similar amino acids and sodium aspartate.

9. The method according to claim 1, wherein the composition is administered orally, intravenously, intraperitoneally, intramuscularly, subcutaneously, intranasally, intradermally, topically or intratracheally.

10. The method according to claim 1, wherein the PSA comprises between 2 and 125 sialic acid units.

11. The method according to claim 10, wherein the PSA comprises at least 10 sialic acid units.

12. The method according to claim 11, wherein the PSA comprises at least 50 sialic acid units.

13. The method according to claim 1, wherein the PSA has an average molecular weight in the range of 2 kDa to 50 kDa.

14. The method according to claim 13, wherein the PSA has an average molecular weight in the range of 5 kDa to 50 kDa.

15. The method according to claim 1, wherein at least two of the sialic acid units is joined to one another through an α-2-8 linkage.

16. The method according to claim 1, wherein at least two of the sialic acid units is joined to one another through an α-2-9 linkage.

17. The method according to claim 1, wherein the PSA is a colominic acid.

* * * * *